United States Patent
Asahina et al.

(10) Patent No.: US 7,514,451 B2
(45) Date of Patent: Apr. 7, 2009

(54) 7-(4-SUBSTITUTED-3-CYCLOPROPYL-AMINOMETHYL-1 PYRROLIDINYL) QUINOLONECARBOXYLIC ACID DERIVATIVE

(75) Inventors: Yoshikazu Asahina, Tochigi (JP); Masaya Takei, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 9 days.

(21) Appl. No.: 10/569,062

(22) PCT Filed: Sep. 8, 2004

(86) PCT No.: PCT/JP2004/013049

§ 371 (c)(1), (2), (4) Date: Mar. 30, 2006

(87) PCT Pub. No.: WO2005/026147

PCT Pub. Date: Mar. 24, 2005

(65) Prior Publication Data

US 2006/0281779 A1 Dec. 14, 2006

(30) Foreign Application Priority Data

Sep. 10, 2003 (JP) ............................. 2003-318897

(51) Int. Cl.
C07D 471/02 (2006.01)
C07D 215/38 (2006.01)
A61K 31/44 (2006.01)
A61K 31/47 (2006.01)

(52) U.S. Cl. ..................... 514/312; 514/300; 546/123; 546/156

(58) Field of Classification Search ................ 514/300, 514/343, 312; 546/123, 156
See application file for complete search history.

(56) References Cited

U.S. PATENT DOCUMENTS

| | | | |
|---|---|---|---|
| 4,292,317 A | 9/1981 | Pesson | |
| 4,398,029 A | 8/1983 | Irikura et al. | |
| 4,604,401 A | 8/1986 | Mich et al. | |
| 4,638,067 A | 1/1987 | Culbertson et al. | |
| 4,665,079 A | 5/1987 | Culbertson et al. | |
| 4,738,968 A * | 4/1988 | Matsumoto et al. | 514/292 |
| 4,771,054 A | 9/1988 | Domagala et al. | |
| 4,771,055 A | 9/1988 | Domagala et al. | |
| 4,777,175 A | 10/1988 | Culbertson et al. | |
| 4,822,801 A | 4/1989 | Domagala et al. | |
| 4,844,902 A | 7/1989 | Grohe | |
| 4,886,810 A | 12/1989 | Matsumoto et al. | |
| 4,894,458 A | 1/1990 | Masuzawa et al. | |
| 4,920,120 A | 4/1990 | Domagala et al. | |
| 4,954,507 A | 9/1990 | Weber et al. | |
| 4,965,273 A | 10/1990 | Weber et al. | |
| 4,988,709 A | 1/1991 | Ogata et al. | |
| 4,997,943 A | 3/1991 | Iwata et al. | |
| 5,023,257 A | 6/1991 | Pöllinger et al. | |
| 5,097,032 A | 3/1992 | Domagala et al. | |
| 5,098,912 A | 3/1992 | Hayakawa et al. | |
| 5,137,892 A | 8/1992 | Chu et al. | |
| 5,140,033 A | 8/1992 | Schriewer et al. | |
| 5,152,986 A | 10/1992 | Lange et al. | |
| 5,164,402 A | 11/1992 | Brighty | |
| 5,173,484 A | 12/1992 | Petersen et al. | |
| 5,229,396 A | 7/1993 | Brighty | |
| 5,252,734 A | 10/1993 | Schriewer et al. | |
| 5,262,417 A | 11/1993 | Gammill et al. | |
| 5,266,569 A | 11/1993 | Brighty | |
| 5,281,612 A | 1/1994 | Domagala et al. | |
| 5,284,842 A | 2/1994 | Petersen et al. | |

(Continued)

FOREIGN PATENT DOCUMENTS

CA 1288712 9/1991

(Continued)

OTHER PUBLICATIONS

Banker, G.S. et al, "Modern Pharmaceutics, 3ed.", Marcel Dekker, New York, 1996, pp. 451 and 596.*

(Continued)

Primary Examiner—D. Margaret Seaman
(74) Attorney, Agent, or Firm—Wenderoth, Lind & Ponack, L.L.P.

(57) ABSTRACT

To provide novel quinolonecarboxylic acid compounds serving as safe, strong antibacterial agents that are effective against drug-resistant bacteria that are less susceptible to conventional antibacterial agents.

There are provided 7-(4-substituted-3-cyclopropylaminomethylpyrrolidinyl)quinolonecarboxylic acid derivatives (such as 1-cyclopropyl-7-[(3S,4S)-3-cyclopropylaminomethyl-4-fluoro-1-pyrrolidinyl]-6-fluoro-1,4-dihydro-8-methoxy-4-oxo-3-quinolinecarboxylic acid) that exhibit strong antibacterial activity against gram-positive bacteria, such as MRSA, PRSP and VRE, while being safe. The compounds are shown by the following general formula (I):

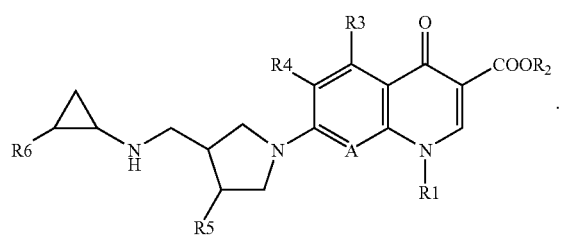

(I)

20 Claims, No Drawings

U.S. PATENT DOCUMENTS

| | | | |
|---|---|---|---|
| 5,290,934 | A | 3/1994 | Ueda et al. |
| 5,336,768 | A | 8/1994 | Albrecht et al. |
| 5,380,874 | A | 1/1995 | Hayakawa et al. |
| 5,385,906 | A | 1/1995 | Gammill et al. |
| 5,391,763 | A | 2/1995 | Brighty |
| 5,409,933 | A | 4/1995 | Kim et al. |
| 5,416,222 | A | 5/1995 | Hayakawa et al. |
| 5,453,422 | A | 9/1995 | Petersen et al. |
| 5,468,742 | A | 11/1995 | Petersen et al. |
| 5,476,950 | A | 12/1995 | Hayakawa et al. |
| 5,495,020 | A | 2/1996 | Ueda et al. |
| 5,563,138 | A | 10/1996 | Ueda et al. |
| 5,578,604 | A | 11/1996 | Himmler et al. |
| 5,585,491 | A | 12/1996 | Domagala et al. |
| 5,591,744 | A | 1/1997 | Ueda et al. |
| 5,646,163 | A | 7/1997 | Demuth, Jr. et al. |
| 5,659,038 | A | 8/1997 | Himmler et al. |
| 5,668,147 | A | 9/1997 | Nakano et al. |
| 5,677,316 | A | 10/1997 | Ao et al. |
| 5,723,648 | A | 3/1998 | Ueda et al. |
| 5,811,576 | A | 9/1998 | Ueda et al. |
| 6,194,434 | B1 * | 2/2001 | Takemura et al. ............ 514/312 |
| 6,329,391 | B1 | 12/2001 | Ledoussal et al. |
| 6,967,205 | B1 | 11/2005 | Abdul-Rahman |
| 2002/0022629 | A1 | 2/2002 | Cagle et al. |
| 2002/0028816 | A1 | 3/2002 | Cagle et al. |
| 2002/0049192 | A1 | 4/2002 | Ledoussal et al. |
| 2002/0173501 | A1 | 11/2002 | Ledoussal et al. |
| 2002/0193370 | A1 | 12/2002 | Cagle et al. |
| 2003/0069253 | A1 | 4/2003 | Cagle et al. |
| 2003/0119848 | A1 | 6/2003 | Takemura et al. |
| 2003/0207862 | A1 | 11/2003 | Ledoussal et al. |
| 2004/0097512 | A1 | 5/2004 | Cagle et al. |
| 2004/0132993 | A1 | 7/2004 | Shetty |
| 2005/0101589 | A1 | 5/2005 | Ledoussal et al. |
| 2005/0209210 | A1 | 9/2005 | Ding et al. |
| 2006/0100436 | A1 | 5/2006 | Ledoussal et al. |

FOREIGN PATENT DOCUMENTS

| | | |
|---|---|---|
| CN | 1583724 | 2/2005 |
| DE | 3632222 | 4/1988 |
| EP | 0 106 489 | 4/1984 |
| EP | 0 106 489 A2 | 4/1984 |
| EP | 0 153 163 A2 | 8/1985 |
| EP | 0 169 710 | 1/1986 |
| EP | 0 172 651 A1 | 2/1986 |
| EP | 0 274 033 | 7/1988 |
| EP | 0 280 915 | 9/1988 |
| EP | 0 284 935 | 10/1988 |
| EP | 0 295 495 | 12/1988 |
| EP | 0 326 916 | 8/1989 |
| EP | 0 337 231 | 10/1989 |
| EP | 0 343 524 | 11/1989 |
| EP | 0 391 132 | 10/1990 |
| EP | 0 523 512 | 1/1993 |
| EP | 0 574 231 | 12/1993 |
| EP | 0 671 391 | 9/1995 |
| EP | 0 900 793 A1 | 3/1999 |
| ES | 2 065 846 | 2/1995 |
| JP | 59-67269 | 4/1984 |
| JP | 60-214773 | 10/1985 |
| JP | 61-43186 | 3/1986 |
| JP | 61-282362 | 12/1986 |
| JP | 62-4284 | 1/1987 |
| JP | 62-019583 | 1/1987 |
| JP | 62-19583 | 1/1987 |
| JP | 62-228063 | 10/1987 |
| JP | 63-166876 | 7/1988 |
| JP | 63-198664 | 8/1988 |
| JP | 1-135770 | 5/1989 |
| JP | 01-230558 | 9/1989 |
| JP | 3-209367 | 9/1991 |
| JP | 6-40814 | 2/1994 |
| JP | 7-300471 | 11/1995 |
| JP | 09-136886 | 5/1997 |
| JP | 2000-319261 | 11/2000 |
| JP | 2003-96075 | 4/2003 |
| WO | 88/02627 | 4/1988 |
| WO | 89/06649 | 7/1989 |
| WO | 90/06307 | 6/1990 |
| WO | 91/02526 | 3/1991 |
| WO | 92/10191 | 6/1992 |
| WO | 93/03026 | 2/1993 |
| WO | 94/10163 | 5/1994 |
| WO | 95/11902 | 5/1995 |
| WO | 96/33992 | 10/1996 |
| WO | 97/40037 A1 | 10/1997 |
| WO | 99/14214 | 3/1999 |
| WO | 00/18386 | 4/2000 |
| WO | 00/18388 | 4/2000 |
| WO | 01/36408 | 5/2001 |
| WO | 01/58876 | 8/2001 |
| WO | 01/89496 | 11/2001 |
| WO | 02/17916 | 3/2002 |
| WO | 03/078439 | 9/2003 |
| WO | 2005/049602 | 6/2005 |
| WO | 2005/070941 | 8/2005 |
| WO | 2006/119694 | 11/2006 |
| WO | 2008/021491 | 2/2008 |

OTHER PUBLICATIONS

Wolff, Manfred E. "Burger's Medicinal Chemistry, 5ed, Part 1", John Wiley & Sons, 1995, pp. 975-977.*

Patani et. al., "Bioisterism: A Rational Approach in Drug Design", Chem. Rev., 96 (8), pp. 3147-3176, 1996.*

Tomita, J Med Chem, vol. 45(25), pp. 5564-5575, 2002.*

D. Bouzard et al. "*Fluoronaphthyridines and Quinolones as Antibacterial Agents. 2. Synthesis and Structure-Activity Relationships of New 1-tert-Butyl 7-Substituted Derivatives*", J. Med. Chem., vol. 33, pp. 1344-1352 (1990).

* cited by examiner

7-(4-SUBSTITUTED-3-CYCLOPROPYL-AMINOMETHYL-1 PYRROLIDINYL) QUINOLONECARBOXYLIC ACID DERIVATIVE

TECHNICAL FIELD

The present invention relates to novel 7-(4-substituted-3-cyclopropylaminomethyl-1-pyrrolidinyl) quinolonecarboxylic acid derivatives that are not only safe and strong antibacterial agents, but are also effective against drug-resistant bacteria that are less susceptible to conventional antibacterial agents. The present invention also relates to salts and hydrates of such quinolonecarboxylic acid derivatives.

TECHNICAL BACKGROUND

Ever since the development of norfloxacin, significant effort has been devoted worldwide to developing quinolone carboxylic acid-based antibacterial agents. These antibacterial agents are now used as an effective cure for infectious diseases.

The recent emergence of drug-resistant bacteria, including methicillin-resistant *Staphylococcus aureus* (MRSA), penicillin-resistant *Streptococcus pneumoniae* (PRSP) and vancomycin-resistant *enterococci* (VRE), poses a serious threat to the treatment of infectious diseases. Most of these drug-resistant bacteria are gram-positive bacteria, which are less susceptible to traditional quinolonecarboxylic acid-based antibacterial agents. Apparently, these antibacterial agents can no longer serve as an effective countermeasure to gram-positive drug-resistant bacteria. The increase in the occurrence of quinolone-resistant *Staphylococcus aureus* (QRSA) resistant to quinolonecarboxylic acid-based antibacterial agents poses another threat to the treatment of infectious diseases.

While certain quinolonecarboxylic acid derivatives having 3-cyclopropylaminomethyl-1-pyrrolidinyl group are known compounds, the antibacterial activity of these compounds against drug-resistant bacteria still remains unclear, as does the safety of the compounds (Patent Documents 1 and 2). No studies have reported the synthesis and the biological activity of quinolonecarboxylic acid derivatives having 4-substituted-3-cyclopropylaminomethyl-1-pyrrolidinyl group.

[Patent Document 1] Japanese Patent Laid-Open Publication No. Sho 59-67269

[Patent Document 2] Pamphlet of WO97/400

DISCLOSURE OF THE INVENTION

Problems to be Solved by the Invention

Accordingly, it is an object of the present invention to provide novel quinolonecarboxylic acid compounds that not only serve as safe, strong antibacterial agents, but are also effective against drug-resistant bacteria that are less susceptible to conventional antibacterial agents.

Means for Solving the Problems

The 7-(4-substituted-3-cyclopropylaminomethyl-1-pyrrolidinyl)quinolonecarboxylic acid derivatives provided by the present invention are safe to use and exhibit strong antibacterial activity against gram positive bacteria, in particular drug-resistant bacteria such as MRSA, PRSP and VRE.

Thus, the present invention comprises the following:

1) A quinolonecarboxylic acid derivative represented by the following general formula (I):

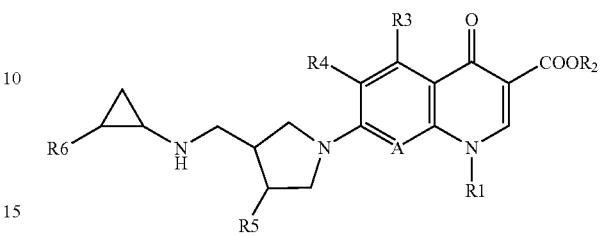

(I)

(wherein R1 is an alkyl group that has 1 to 6 carbon atoms and may or may not be substituted with 1 or 2 or more halogen atoms, a cycloalkyl group that has 3 to 6 carbon atoms and may or may not be substituted with 1 or 2 or more halogen atoms, or an aryl or heteroaryl group that may or may not be substituted with 1 or 2 or more substituents that are each independently a halogen atom or an amino group; R2 is a hydrogen atom, an alkyl group having 1 to 3 carbon atoms, a pharmaceutically acceptable cation, or a functional group acceptable as a prodrug; R3 is a hydrogen atom, a halogen atom, a hydroxyl group, an amino group or an alkyl group having 1 to 3 carbon atoms; R4 is a hydrogen atom or a halogen atom; R5 is an alkyl group having 1 to 3 carbon atoms, a fluoromethyl group, a trifluoromethyl group or a fluorine atom; R6 is a hydrogen atom or a fluorine atom; and A is a nitrogen atom or =C—X (where X is a hydrogen atom, halogen atom, or alkyl or alkoxyl group that has 1 to 3 carbon atoms and may or may not be substituted with 1 or 2 or more amino groups, cyano groups or halogen atoms.)), and salts and hydrates thereof.

2) The compound according to 1) above, wherein in the general formula (I), R1 is a cyclopropyl group, 2-fluorocyclopropyl group, ethyl group, 2-fluoroethyl group, 4-fluorophenyl group or 2,4-difluorophenyl group, and salts and hydrates thereof.

3) The compound according to 1) above, wherein in the general formula (I), R1 is a cyclopropyl group, 2-fluorocyclopropyl group, ethyl group, 2-fluoroethyl group, 4-fluorophenyl group or 2,4-difluorophenyl group, and R4 is a hydrogen atom or a fluorine atom, and salts and hydrates thereof.

4) The compound according to 1) above, wherein in the general formula (I), R1 is a cyclopropyl group, 2-fluorocyclopropyl group, ethyl group, 2-fluoroethyl group, 4-fluorophenyl group or 2,4-difluorophenyl group; R4 is a hydrogen atom or a fluorine atom; and A is a nitrogen atom or =C—X (where X is a hydrogen atom, halogen atom, methoxy group, difluoromethoxy group or methyl group), and salts and hydrates thereof.

5) The compound according to 1) above, wherein in the general formula (I), R1 is a cyclopropyl group, 2-fluorocyclopropyl group, ethyl group, 2-fluoroethyl group, 4-fluorophenyl group or 2,4-difluorophenyl group; R4 is a hydrogen atom or a fluorine atom; R5 is a fluorine atom or a methyl group; R6 is a hydrogen atom or a fluorine atom; and A is a nitrogen atom or =C—X (where X is a hydrogen atom, halogen atom, methoxy group, difluoromethoxy group or methyl group), and salts and hydrates thereof.

6) An antibacterial agent containing as an active ingredient the compound according to 1) to 5) above or a salt or a hydrate thereof.

With regard to the general formula (1), the term "pharmaceutically acceptable cation" refers to sodium ion, potassium ion, magnesium ion, calcium ion and ammonium ion, and the term "functional group acceptable as a prodrug" refers to pivaloyloxymethyl group, acetoxymethyl group, phthalidinyl group, indanyl group, methoxymethyl group and 5-methyl-2-oxo-1,3-dioxolene-4-yl group. The term "halogen atom" refers to fluorine, chlorine, bromine and iodine.

The term "alkyl group having 1 to 6 carbon atoms" refers to ethyl group, propyl group, 2-propyl group, butyl group, 2-butyl group, 1,1-dimethylethyl group, pentyl group and hexyl group. The term "cycloalkyl group having 3 to 6 carbon atoms" refers to cyclopropyl group, cyclobutyl group, cyclopentyl group and cyclohexyl group. The term "alkyl group having 1 to 3 carbon atoms" refers to methyl group, ethyl group, propyl group, 2-propyl group, and cyclopropyl group. The term "alkoxy group having 1 to 3 carbon atoms" refers to methoxy group, ethoxy group, propoxy group, 2-propoxy group and cyclopropyloxy group. The term "aryl group" refers to phenyl group and naphthyl group. The term "heteroaryl group" refers to pyridyl group, pyrimidinyl group, pyradinyl group, pyridadinyl group, thiazolyl group, and imidazoyl group.

Advantage of the Invention

The compounds of the present invention represented by the general formula above are novel compounds. They are safe to use and exhibit strong antibacterial activity against gram positive bacteria, in particular drug-resistant bacteria such as MRSA, PRSP and VRE.

Best Mode for Carrying Out the Invention

Examples of the quinolonecarboxylic acid derivatives represented by the above-described general formula (I) include 1-cyclopropyl-7-[(3S,4S)-3-cyclopropylaminomethyl-4-fluoro-1-pyrrolidinyl]-6-fluoro-1,4-dihydro-8-methoxy-4-oxo-3-quinolinecarboxylic acid, 1-cyclopropyl-7-[(3S,4S)-3-cyclopropylaminomethyl-4-fluoro-1-pyrrolidinyl]-1,4-dihydro-8-methoxy-4-oxo-3-quinolinecarboxylic acid, 1-cyclopropyl-7-[(3S,4S)-3-cyclopropylaminomethyl-4-fluoro-1-pyrrolidinyl]-6-fluoro-8-difluoromethoxy-1,4-dihydro-4-oxo-3-quinolinecarboxylic acid, 1-cyclopropyl-7-[(3S,4S)-3-cyclopropylaminomethyl-4-fluoro-1-pyrrolidinyl]-8-difluoromethoxy-1,4-dihydro-4-oxo-3-quinolinecarboxylic acid, 1-cyclopropyl-7-(trans-3-cyclopropylaminomethyl-4-methyl-1-pyrrolidinyl-6-fluoro-1,4-dihydro-8-methoxy-4-oxo-3-quinolinecarboxylic acid, 1-cyclopropyl-7-(trans-3-cyclopropylaminomethyl-4-trifluoromethyl-1-pyrrolidinyl-6-fluoro-1,4-dihydro-8-methoxy-4-oxo-3-quinolinecarboxylic acid, 1-cyclopropyl-7-[(3S,4R)-3-cyclopropylaminomethyl-4-methyl-1-pyrrolidinyl]-1,4-dihydro-8-methoxy-4-oxo-3-quinolinecarboxylic acid, 1-cyclopropyl-7-[(3R,4S)-3-cyclopropylaminomethyl-4-methyl-1-pyrrolidinyl]-1,4-dihydro-8-methoxy-4-oxo-3-quinolinecarboxylic acid, 1-cyclopropyl-7-[(3S,4R)-3-cyclopropylaminomethyl-4-fluoro-1-pyrrolidinyl]-6-fluoro-1,4-dihydro-8-methoxy-4-oxo-3-quinolinecarboxylic acid, 1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid, 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-8-methoxy-3-quinolinecarboxylic acid, 7-[(3S,4S)-3-cyclopropylaminomethyl-4-fluoro-1-pyrrolidinyl]-6-fluoro-1-[(1R,2S)-2-fluorocyclopropyl]-8-difluoromethoxy-1,4-dihydro-4-oxo-3-quinolinecarboxylic acid, 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-8-methyl-3-quinolinecarboxylic acid, 7-[(3S,4S)-3-cyclopropylaminomethyl-4-fluoro-1-pyrrolidinyl]-1-[(1R,2S)-2-fluorocyclopropyl]-1,4-dihydro-4-oxo-8-methoxy-3-quinolinecarboxylic acid, 7-[(3S,4S)-3-cyclopropylaminomethyl-4-fluoro-1-pyrrolidinyl]-1-ethyl-6-fluoro-1,4-dihydro-8-methoxy-4-oxo-3-quinolinecarboxylic acid, 7-[(3S,4S)-3-cyclopropylaminomethyl-4-fluoro-1-pyrrolidinyl]-6-fluoro-1-(2-fluoroethyl)-1,4-dihydro-8-methoxy-4-oxo-3-quinolinecarboxylic acid, 1-cyclopropyl-7-[(3S,4R)-3-cyclopropylaminomethyl-4-methyl-1-pyrrolidinyl]-6-fluoro-1,4-dihydro-8-methoxy-4-oxo-3-quinolinecarboxylic acid, 1-cyclopropyl-7-[(3S,4S)-3-cyclopropylaminomethyl-4-methyl-1-pyrrolidinyl]-6-fluoro-1,4-dihydro-8-methoxy-4-oxo-3-quinolinecarboxylic acid, 1-cyclopropyl-7-[(3R,4S)-3-cyclopropylaminomethyl-4-methyl-1-pyrrolidinyl]-6-fluoro-1,4-dihydro-8-methoxy-4-oxo-3-quinolinecarboxylic acid, 1-cyclopropyl-7-[(3R,4R)-3-cyclopropylaminomethyl-4-methyl-1-pyrrolidinyl]-6-fluoro-1,4-dihydro-8-methoxy-4-oxo-3-quinolinecarboxylic acid, 7-[(3S,4R)-3-cyclopropylaminomethyl-4-methyl-1-pyrrolidinyl]-6-fluoro-1-[(1R,2S)-2-fluorocyclopropyl]-1,4-dihydro-8-methoxy-4-oxo-3-quinolinecarboxylic acid, 7-[(3S,4S)-3-cyclopropylaminomethyl-4-methyl-1-pyrrolidinyl]-6-fluoro-1-[(1R,2S)-2-fluorocyclopropyl]-1,4-dihydro-8-methoxy-4-oxo-3-quinolinecarboxylic acid, 7-[(3S,4S)-3-cyclopropylaminomethyl-4-fluoro-1-pyrrolidinyl]-1-ethyl-6-fluoro-1,4-dihydro-4-oxo-3-quinoline carboxylic acid, 7-[(3S,4S)-3-cyclopropylaminomethyl-4-fluoro-1-pyrrolidinyl]-1-ethyl-6,8-difluoro-1,4-dihydro-4-oxo-3-quinolinecarboxylic acid, 7-[(3S,4S)-3-cyclopropylaminomethyl-4-fluoro-1-pyrrolidinyl]-6-fluoro-1-(2-fluoroethyl)-1,4-dihydro-4-oxo-3-quinolinecarboxylic acid, 7-[(3S,4S)-3-cyclopropylaminomethyl-4-fluoro-1-pyrrolidinyl]-6,8-difluoro-1-(2-fluoroethyl)-1,4-dihydro-4-oxo-3-quinolinecarboxylic acid, 7-[(3S,4S)-3-cyclopropylaminomethyl-4-fluoro-1-pyrrolidinyl]-6-fluoro-1-(2,4-difluorophenyl)-1,4-dihydro-4-oxo-1,8-naphthyridine-3-carboxylic acid, 7-[(3S,4S)-3-cyclopropylaminomethyl-4-fluoro-1-pyrrolidinyl]-6-fluoro-1-(2,4-difluorophenyl)-1,4-dihydro-4-oxo-3-quinolinecarboxylic acid, 1-cyclopropyl-7-[(3S,4S)-3-cyclopropylaminomethyl-4-fluoro-1-pyrrolidinyl]-6-fluoro-1,4-dihydro-4-oxo-1,8-naphthyridine-3-carboxylic acid, 1-cyclopropyl-7-[(3S,4S)-3-cyclopropylaminomethyl-4-fluoro-1-pyrrolidinyl]-6-fluoro-1,4-dihydro-4-oxo-3-quinolinecarboxylic acid, 1-cyclopropyl-7-[(3S,4S)-3-cyclopropylaminomethyl-4-fluoro-1-pyrrolidinyl]-6,8-difluoro-1,4-dihydro-4-oxo-3-quinolinecarboxylic acid, 8-chloro-1-cyclopropyl-7-[(3S,4S)-3-cyclopropylaminomethyl-4-fluoro-1-pyrrolidinyl]-6-fluoro-1,4-dihydro-4-oxo-3-quinolinecarboxylic acid, 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-1,8-naphthyridine-3-carboxylic acid, 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-3-quinolinecarboxylic acid, 7-[(3S,4S)-3-cyclopropylaminomethyl-4-fluoro-1-pyrrolidinyl]-6,8-difluoro-1-[(1R,2S)-2-fluorocyclopropyl]-1,4-dihydro-4-oxo-3-quinolinecarboxylic acid, 8-chloro-7-[(3S,4S)-3- cyclopropylaminomethyl-4-fluoro-1-pyrrolidinyl]-6-fluoro-1-[(1R,2S)-2-fluorocyclopropyl]-1,4-dihydro-4-oxo-3-quinolinecarboxylic acid, 5-amino-1-cyclopropyl-7-[(3S,4S)-3-cyclopropylaminomethyl-4-fluoro-1-pyrrolidinyl]-6-fluoro-1,4-dihydro-8-methoxy-4-oxo-3-quinolinecarboxylic acid, 5-amino-1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid, 5-amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methoxy-4-oxo-3-quinolinecarboxylic acid, 5-amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methyl-4-oxo-3-quinolinecarboxylic acid, 7-[(3S,4S)-3-cyclopropylaminomethyl-4-fluoro-1-pyrrolidinyl]-6-fluoro-1,4-dihydro-1-(1,1-dimethylethyl)-4-oxo-1,8-naphthyridine-3-carboxylic acid, 7-[(3S,4S)-3-cyclopropylaminomethyl-4-fluoro-1-pyrrolidinyl]-6-fluoro-1,4-dihydro-1-(1,1-dimethylethyl)-4-oxo-3-quinolinecarboxylic acid, 7-[(3S,4S)-3-cyclopropylaminomethyl-4-fluoro-1-pyrrolidinyl]-6,8-difluoro-1,4-dihydro-1-(1,1-dimethylethyl)-4-oxo-3-quinolinecarboxylic acid, and salts and hydrates thereof.

One exemplary process for producing the compound of the invention represented by the general formula (I) is described below.

A compound represented by the following general formula (II):

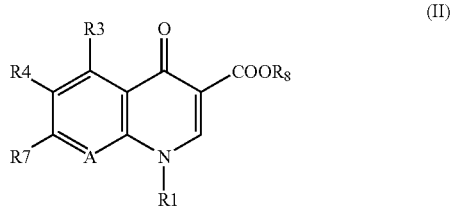

(II)

[wherein R1, R3, R4 and A are as defined with reference to the general formula (I); R7 is a halogen atom, such as fluorine, chlorine, bromine and iodine; and R8 is a hydrogen atom, an alkyl group having 1 to 6 carbon atoms, benzyl group or a moiety represented by the following general formula (III):

(III)

(wherein R9 and R10 are each independently a fluorine atom or a lower alkylcarbonyloxy group)] is reacted with a compound represented by the following general formula (IV):

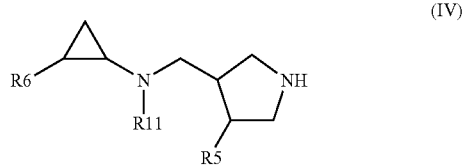

(IV)

(wherein R5 and R6 are as defined with reference to the general formula (I); and R11 is a hydrogen atom or a protective group of the nitrogen atom, such as t-buthoxycarbonyl group) or an acid-addition salt thereof. If necessary, the boron chelate, ester or the nitrogen-protecting group may be removed from the resulting product to give the desired compound.

The reaction of the compound of the general formula (II) with the compound of the general formula (IV) is carried out in the absence or presence of a solvent and in the presence of an acid receptor agent. Examples of the solvent are alcohols, acetonitrile, dimethylsulfoxide, N,N-dimethylformamide, N,N-dimethylacetamide, N-methylpyrrolidone, tetrahydrofuran, dioxane, benzene, and toluene. Examples of the acid receptor agent are carbonates or bicarbonates of alkali metals and alkaline earth metals and basic organic compounds such as triethylamine, diazabicyclo-7-undecene and pyridine. The reaction is typically carried out at a temperature of room temperature to 200° C., and preferably at a temperature of 25° C. to 150° C., and comes to an end in a time period of 30 min to 48 hours, typically in a time period of 30 min to 15 hours.

If desired, the compounds represented by the general formula (I) can be converted to their salts by ordinary techniques. Examples of such salts are salts formed with inorganic acids such as hydrochloric acid, sulfuric acid and phosphoric acid, salts formed with organic acids such as methanesulfonic acid, lactic acid, oxalic acid and acetic acid, and salts formed with sodium, potassium, magnesium, calcium, aluminum, cerium, chromium, cobalt, copper, iron, zinc, platinum and silver.

The compound of the present invention can be administered to humans or animals in pharmaceutically well-known forms through pharmaceutically well-known routes. For example, it can be administered orally or non-orally in the form of powder, tablets, capsules, ointment, injection, syrups, solutions, eyedrops and suppositories.

The compounds of the present invention and the salts thereof may have multiple optical isomers with two or more asymmetric carbon atoms, and all of such optical isomers and diastereomers as well as mixtures and racemic mixtures thereof in a given ratio are encompassed by the invention.

EXAMPLES

Tests performed on compounds of the present invention and exemplary processes for producing the compounds will now be described in detail with reference to examples.

Reference Example 1

Synthesis of trans-3-cyclopropylaminomethyl-4-methylpyrrolidine

Step 1:

trans-1-Benzyl-4-methyl-3-pyrrolidine carboxylic acid (4.04 g) was dissolved in dichloromethane (50 mL). To this solution, 1,1'-carbonyl bis-1H-imidazole (3.58 g) was added and the mixture was stirred at room temperature for 1 hour. While the mixture was chilled in an ice bath, cyclopropylamine (1.53 mL) in dichloromethane (15 mL) was added drop wise and the mixture was stirred at room temperature for 3 hours. Subsequently, the reaction mixture was washed with water, dried over anhydrous sodium sulfate, and concentrated under reduced pressure. The residue was crystallized from a hexane/diisopropyl ether mixture, and the crystals were filtered, washed with a hexane/diisopropyl ether mixture, and dried under reduced pressure to give trans-1-benzyl-N-cyclopropyl-4-methyl-3-pyrrolidine carboxamide as white crystals (4.07 g).

MP: 81-83° C.
MS (EI) m/z: 258(M$^+$).

Step 2:

trans-1-Benzyl-N-cyclopropyl-4-methyl-3-pyrrolidine carboxamide (3.80 g) was suspended in anhydrous tetrahydrofurane (85 mL). To this suspension, a 1M tetrahydrofuran solution of borane-tetrahydrofuran complex (58.8 mL) was added and the mixture was refluxed for 8 hours. Subsequently, a 2 mol/L aqueous solution of sodium hydroxide (35 mL) was added and the mixture was refluxed for 4 hours. The reaction mixture was then concentrated under reduced pressure and the residue was extracted with toluene (2×100 mL). The organic layers were combined, washed with water, dried over anhydrous sodium sulfate, and concentrated under reduced pressure. The resulting residue was dissolved in dichloromethane (50 mL), followed by addition of di-tert-butyldicarbonate (3.53 g) and stirring at room temperature for 4 hours. The mixture was then concentrated under reduced pressure and the residue was purified by silica gel column chromatography (hexane: ethyl acetate=4:1->1:1) to give trans-1-benzyl-3-[[(N-tert-butoxycarbonyl-N-cyclopropyl) amino]methyl]-4-methylpyrrolidine (3.07 g) as a colorless oil.

MS (FAB$^+$) m/z: 345 (MH$^+$).
HRMS (FAB$^+$)
Calcd for $C_{21}H_{33}N_2O_2$ (MH$^+$): 345.2542. Found: 345.2505.

Step 3:

trans-1-Benzyl-3-[[(N-tert-butoxycarbonyl-N-cyclopropyl)amino]methyl]-4-methylpyrrolidine (3.00 g) was dissolved in ethanol (50 mL). To this solution, 7.5% palladium carbon (300 mg) was added and the mixture was stirred at room temperature for 6 hours under a hydrogen pressure of 3.9×10$^5$ Pa. Subsequently, the catalyst was filtered and washed with ethanol and the filtrate was combined with the washings. The residue was then dried under reduced pressure to give trans-3-[[(N-tert-butoxycarbonyl-N-cyclopropyl) amino]methyl]-4-methylpyrrolidine as a pale brown oil (2.12 g).

MS (FAB$^+$) m/z: 255 (MH$^+$)
HRMS (FAB$^+$)
Calcd for $C_{14}H_{27}N_2O_2$(MH$^+$): 255.2073. Found: 255.2079.

Step 4:

trans-3-[[(N-tert-Butoxycarbonyl-N-cyclopropyl)amino] methyl]-4-methylpyrrolidine (2.07 g) was dissolved in dichloromethane (10 mL). While the solution was chilled in an ice bath, trifluoroacetic acid (5 mL) was added and the mixture was stirred at room temperature for 2 hours. The reaction mixture was then concentrated under reduced pressure. The resulting residue was dissolved in tetrahydrofuran (6 mL) and the solution was allowed to stand at room temperature for 13 hours. The resulting crystals were filtered, washed with tetrahydrofuran, and dried under reduced pressure to give 2.47 g of trans-3-cyclopropylaminomethyl-4-methylpyrrolidine trifluoroaceate. This salt (2.37 g) was dissolved in water (5 mL) and a 20% aqueous solution of sodium hydroxide was added to adjust the solution to pH 14. The mixture was then extracted with diethyl ether (2×50 mL) and the diethyl ether layers were combined, dried over anhydrous sodium sulfate, and concentrated under reduced pressure. The resulting residue was purified by distillation under reduced pressure to give trans-3-cyclopropylaminomethyl-4-methylpyrrolidine (660 mg).

$^1$H NMR(CDCl$_3$): δ 0.30-0.37 (m, 2H), 0.41-0.45(m, 2H), 1.04(d, J=6.3 Hz, 3H), 1.66-1.76(m, 4H), 2.08-2.13(m, 1H), 2.46(dd, J=7.3 Hz, 10.7 Hz, 1H), 2.57(dd, J=8.3 Hz, 11.7 Hz, 1H), 2.63(dd, J=6.3 Hz, 10.7 Hz, 1H), 2.80 (dd, J=5.4 Hz, 11.7 Hz, 1H), 3.10 (dd, J=6.8 Hz, 10.7 Hz, 1H), 3.14 (dd, J=7.3 Hz, 10.7 Hz, 1H).

Elemental analysis (%)

Calcd for $C_9H_{18}N_2$.2CF$_3$COOH: C, 40.84; H, 5.27; N, 7.33. Found: C, 40.90; H, 5.47; N, 7.37.

Reference Example 2

Synthesis of (3R,4R)-3-cyclopropylaminomethyl-4-methylpyrrolidine

Step 1:

(3R,4R)-1-Benzyl-4-methyl-3-pyrrolidine carboxylic acid (6.27 g) was suspended in dichloromethane (250 mL). To this suspension, cyclopropylamine (1.76 mL) and 1-ethyl-(3-dimethylaminopropyl)carbodiimide hydrochloride (12.2 g) were sequentially added and the mixture was stirred at room temperature for 4 hours. Subsequently, the reaction mixture was washed with water, dried over anhydrous sodium sulfate, and concentrated under reduced pressure. The residue was purified by silica gel column chromatography (ethyl acetate: methanol=10:1) to give (3R,4R)-1-benzyl-N-cyclopropyl-4-methyl-3-pyrrolidine carboxamide (3.32 g) as white crystals.

MS (EI) m/z: 258 (M$^+$)

Elemental analysis (%)

Calcd for $C_{16}H_{22}N_2O$: C, 74.38; H, 8.58; N, 10.84. Found: C, 74.46; H, 8.67; N, 10.72.

Step 2:

Using (3R,4R)-1-benzyl-N-cyclopropyl-4-methyl-3-pyrrolidine carboxamide (5.52 g), the same procedure was followed as in Step 2 of Reference Example 1 to give (3R,4R)-1-benzyl-3-[[(N-tert-butoxycarbonyl-N-cyclopropyl)amino] methyl]-4-methylpyrrolidine (4.16 g) as a pale brown oil.

MS (FAB$^+$) m/z: 345 (MH$^+$)
HRMS (FAB$^+$)
Calcd for $C_{21}H_{33}N_2O_2$(MH$^+$): 345.2542. Found: 345.2585.

Step 3:

Using (3R,4R)-1-benzyl-3-[[(N-tert-butoxycarbonyl-N-cyclopropyl)amino]methyl]-4-methylpyrrolidine (4.00 g), the same procedure was followed as in Step 3 of Reference Example 1 to give (3R,4R)-3-[[(N-tert-butoxycarbonyl-N-cyclopropyl)amino]methyl]-4-methylpyrrolidine (2.88 g).

MS (FAB$^+$) m/z: 255 (MH$^+$)
HRMS (FAB$^+$)
Calcd for $C_{14}H_{27}N_2O_2$(MH$^+$): 255.2073. Found: 255.2070.

Step 4:

Using (3R,4R)-3-[[(N-tert-butoxycarbonyl-N-cyclopropyl)amino]methyl]-4-methylpyrrolidine (2.78 g), the same procedure was followed as in Step 4 of Reference Example 1 to give (3R,4R)-3-cyclopropylaminomethyl-4-methylpyrrolidine (730 mg).

Specific rotation: +74.6° (c=0.648, methanol).

Elemental analysis (%)
Calcd for $C_9H_{18}N_2 \cdot 2CF_3COOH$: C, 40.84; H, 5.27; N, 7.33. Found: C, 40.73; H, 5.26; N, 7.36.

Reference Example 3

Synthesis of (3S,4S)-3-cyclopropylaminomethyl-4-methylpyrrolidine

Step 1:
Using (3S,4S)-1-benzyl-4-methyl-3-pyrrolidine carboxylic acid (14.5 g), the same procedure was followed as in Step 1 of Reference Example 2 to give (3S,4S)-1-benzyl-N-cyclopropyl-4-methyl-3-pyrrolidine carboxamide as pale brown crystals (6.33 g).

MS (EI) m/z: 258 (M$^+$).

Elemental analysis (%)
Calcd for $C_{16}H_{22}N_2O$: C, 74.38; H, 8.58; N, 10.84.
Found: C, 74.64; H, 8.66; N, 10.71.

Step 2:
Using (3S,4S)-1-benzyl-N-cyclopropyl-4-methyl-3-pyrrolidine carboxamide (6.13 g), the same procedure was followed as in Step 2 of Reference Example 1 to give (3S,4S)-1-benzyl-3-[[(N-tert-butoxycarbonyl-N-cyclopropyl)amino]methyl]-4-methylpyrrolidine (4.67 g) as a pale brown oil.

MS (FAB$^+$) m/z: 345 (MH$^+$).
HRMS (FAB$^+$)
Calcd for $C_{21}H_{33}N_2O_2$(MH$^+$): 345.2542.
Found: 345.2547.

Step 3:
Using (3S,4S)-1-benzyl-3-[[(N-tert-butoxycarbonyl-N-cyclopropyl)amino]methyl]-4-methylpyrrolidine (4.47 g), the same procedure was followed as in Step 3 of Reference Example 1 to give (3S,4S)-3-[[(N-tert-butoxycarbonyl-N-cyclopropyl)amino]methyl]-4-methylpyrrolidine (3.05 g).

MS (FAB$^+$) m/z: 255 (MH$^+$).
HRMS (FAB$^+$)
Calcd for $C_{14}H_{27}N_2O_2$(MH$^+$): 255.2073. Found: 255.2075.

Step 4:
Using (3S,4S)-3-[[(N-tert-butoxycarbonyl-N-cyclopropyl)amino]methyl]-4-methylpyrrolidine (2.85 g), the same procedure was followed as in Step 4 of Reference Example 1 to give (3S,4S)-3-cyclopropylaminomethyl-4-methylpyrrolidine (1.21 g).

Specific rotation: −74.5° (c=0.62, methanol).

elemental analysis (%)
Calcd for $C_9H_{18}N_2 \cdot 2CF_3COOH$: C, 40.84; H, 5.27; N, 7.33. Found: C, 40.80; H, 5.18; N, 7.39.

Reference Example 4

Synthesis of cis-3-cyclopropylaminomethyl-4-methylpyrrolidine

Step 1:
cis-1-Benzyl-3-hydroxy-4-methylpyrrolidine (6.81 g) was dissolved in dichloromethane (70 mL). While the solution was chilled in a dry ice/acetone bath, triethylamine (5.21 mL) was added, followed by dropwise addition of methanesulfonyl chloride (2.89 mL) and stirring for 1 hour. Subsequently, water (50 mL) was added and the mixture was allowed to warm to room temperature. The dichloromethane layer was separated and the aqueous layer was extracted with dichloromethane (50 mL). The dichloromethane layers were combined, washed with water, dried over anhydrous sodium sulfate and concentrated under reduced pressure. The resulting residue was dissolved in acetonitrile (180 mL). To this solution, tetrabutylammonium cyanide (23.9 g) was added and the mixture was refluxed for 7 hours. Subsequently, the reaction mixture was concentrated under reduced pressure and the residue was dissolved in ethyl acetate (300 mL). This solution was washed with water, dried over anhydrous sodium sulfate, and concentrated under reduced pressure. The residue was then purified by silica gel column chromatography (hexane: ethyl acetate=1:1) to give cis-1-benzyl-4-methyl-3-pyrrolidinecarbonitrile as a brown oil (4.61 g).

IR (neat): 2240, 1496, 1454 cm$^{-1}$.
MS (EI) m/z: 200 (M$^+$).

Step 2:
Lithium aluminum hydride (80%, 3.89 g) was suspended in diethyl ether (90 mL). While the suspension was chilled in an ice bath, cis-1-benzyl-4-methyl-3-pyrrolidinecarbonitrile (4.11 g) in diethyl ether (25 mL) was added dropwise and the mixture was stirred at room temperature for 1 hour. Subsequently, a saturated aqueous solution of sodium bicarbonate (8 mL) was carefully added dropwise while the reaction mixture was chilled in an ice water bath. The reaction mixture was then diluted with diethyl ether (100 mL) and the insoluble material was filtered and was washed with diethyl ether. The filtrate and the washings were combined and the organic layer was concentrated under reduced pressure. The resulting residue was purified by silica gel column chromatography (hexane: ethyl acetate=1:1->ethyl acetate: methanol=10:1) to give cis-1-benzyl-4-methyl-3-aminomethylpyrrolidine as a pale yellow oil (2.35 g).

$^1$H NMR(CDCl$_3$): δ 0.94 (d, J=7.3 Hz, 3H), 1.09-1.66 (br, 2H), 2.03(dd, J=7.3 Hz, 9.3 Hz, 1H), 2.11-2.26 (m, 2H), 2.31-2.42 (m, 1H), 2.58 (dd, J=8.3 Hz, 12.2 Hz, 1H), 2.82 (dd, J=5.9 Hz, 12.2 Hz, 1H), 2.96-3.02 (m, 2H), 3.60 (s, 2H), 7.21-7.35 (m, 5H).

Step 3:
cis-1-Benzyl-4-methyl-3-aminomethylpyrrolidine (1000 mg) was dissolved in methanol (10 mL). While this solution was chilled in an ice water bath, benzaldehyde (0.50 mL) was added dropwise and the mixture was stirred at room temperature for 1 hour. Subsequently, sodium cyanoborohydride (184 mg) was added and the mixture was stirred at room temperature for 1.5 hours, followed by addition of a second portion of sodium cyanoborohydride (123 mg) and then further stirring for 5.5 hours. To the resulting mixture, a 2 mol/L aqueous solution of sodium hydroxide (5 mL) was added and the mixture was refluxed for 2 hours. Subsequently, the reaction mixture was concentrated under reduced pressure and the residue was extracted with toluene (2×30 mL). The toluene layers were combined, washed with water, dried over anhydrous sodium sulfate, and concentrated under reduced pressure. The resulting residue was purified by silica gel column chromatography (hexane: ethyl acetate=4:1) to give cis-1-benzyl-3-benzylaminomethyl-4-methylpyrrolidine as a pale yellow oil (690 mg).

MS (EI) m/z: 294 (M$^+$)
HRMS (EI)
Calcd for $C_{20}H_{26}N_2$(M$^+$): 294.2096. Found: 294.2110.

Step 4:

Cis-1-benzyl-3-benzylaminomethyl-4-methylpyrrolidine (680 mg) was dissolved in methanol (7 mL). To this solution, molecular sieves 3A (700 mg), acetic acid (1.32 mL), [1-(ethoxycyclopropyl)oxy]trimethylsilane (1.85 mL) and sodium cyanoborohydride (435 mg) were added and the mixture was refluxed for 4 hours. Subsequently, the insoluble material in the mixture was filtered and was washed with methanol. The filtrate and the washings were combined and the organic layer was concentrated under reduced pressure. To the resulting residue, water (5 mL) was added followed by a 2 mol/L aqueous solution of sodium hydroxide to make the mixture basic and then the mixture was extracted with toluene (2×50 mL). The toluene layers were combined, washed with water, dried over anhydrous sodium sulfate, and concentrated under reduced pressure. The resulting residue was purified by silica gel column chromatography (hexane: ethyl acetate=4:1) to give cis-1-benzyl-3-(N-benzyl-N-cyclopropyl)aminomethyl-4-methylpyrrolidine as a colorless oil (648 mg).

MS (EI) m/z: 334 (M$^+$)

HRMS (EI)

Calcd for $C_{23}H_{30}N_2(M^+)$: 334.2409. Found: 334.2403.

Step 5:

cis-1-Benzyl-3-(N-benzyl-N-cyclopropyl)aminomethyl-4-methylpyrrolidine (640 mg) was dissolved in ethanol (10 mL). To this solution, 10% palladium carbon (500 mg) and chloroform (0.77 mL) were added and the mixture was stirred at 50° C. for 7 hours under a hydrogen pressure of $3.9 \times 10^5$ Pa. The catalyst in the mixture was filtered and washed with ethanol. The filtrate and the washings were combined and the organic layer was concentrated under reduced pressure. To the resulting residue, water (2 mL) was added followed by a 2 mol/L aqueous solution of sodium hydroxide to make the mixture basic. The mixture was then salted out with sodium chloride and was extracted with diethyl ether (2×25 mL). The diethyl ether layers were combined, dried over anhydrous sodium sulfate, and concentrated under reduced pressure. The resulting residue was purified by silica gel column chromatography (hexane: ethyl acetate=4:1->dichloromethane:methanol=10:1) to give cis-3-cyclopropylaminomethyl-4-methylpyrrolidine as a pale brown oil (124 mg).

MS (CI$^+$) m/z: 155 (MH$^+$)

HRMS (CI$^+$)

Calcd for $C_9H_{19}N_2(MH^+)$: 155.1548. Found: 155.1553.

Reference Example 5

Synthesis of (3R,4S)-3-cyclopropylaminomethyl-4-methylpyrrolidine

Step 1:

(3R,4S)-1-Benzyl-3-hydroxy-4-methylpyrrolidine (4.00 g) was dissolved in dichloromethane (40 mL). While the solution was chilled in a dry ice/acetone bath, triethylamine (3.06 mL) was added, followed by dropwise addition of methanesulfonyl chloride (1.70 mL) and stirring for 1 hour. Subsequently, water (40 mL) was added and the mixture was allowed to warm to room temperature. The dichloromethane layer was separated and the aqueous layer was extracted with dichloromethane (40 mL). The dichloromethane layers were combined, washed with water, dried over anhydrous sodium sulfate and concentrated under reduced pressure. The resulting residue was dissolved in N,N-dimethylformamide (120 mL), followed by the addition of tetrabutylammonium cyanide (5.53 g) and sodium cyanide (2.05 g) and stirring at 80° C. for 13 hours. Subsequently, the reaction mixture was concentrated under reduced pressure. Water (50 mL) was then added to the resulting residue and the mixture was extracted with diethyl ether (2×200 mL). The diethyl ether layers were combined, washed with saturated brine, dried over anhydrous sodium sulfate, and concentrated under reduced pressure. The residue was purified by silica gel column chromatography (hexane: ethyl acetate=4:1) to give (3R,4S)-1-benzyl-4-methyl-3-pyrrolidinecarbonitrile as a brown oil (3.32 g).

$^1$H NMR(CDCl$_3$): δ 1.22 (d, J=7.3 Hz, 3H), 2.12 (dd, J=8.3 Hz, 9.3 Hz, 1H), 2.45-2.57 (m, 1H), 2.60-2.67 (m, 1H), 2.99 (dd, J=7.3 Hz, 9.3 Hz, 1H), 3.09-3.19 (m, 2H), 3.62 (s, 2H), 7.25-7.35 (m, 5H).

MS(EI)m/z: 200 (M$^+$)

Step 2:

Using (3R,4S)-1-benzyl-4-methyl-3-pyrrolidinecarbonitrile (3.20 g), the same procedure was followed as in Step 2 of Reference Example 4 to give (3S,4S)-1-benzyl-4-methyl-3-aminomethylpyrrolidine (2.98 g).

$^1$H NMR(CDCl$_3$): δ 0.94 (d, J=7.3 Hz, 3H), 2.03 (dd, J=7.3 Hz, 9.3 Hz, 1H), 2.11-2.26 (m, 2H), 2.31-2.43 (m, 1H), 2.58 (dd, J=8.3 Hz, 12.2 Hz, 1H), 2.82 (dd, J=5.9 Hz, 12.2 Hz, 1H), 2.97-3.02 (m, 2H), 3.60 (s,2H), 7.22-7.33 (m, 5H).

Step 3:

Using (3S,4S)-1-benzyl-4-methyl-3-aminomethylpyrrolidine (2.80 g), the same procedure was followed as in Step 3 of Reference Example 4 to give (3R,4S)-1-benzyl-3-benzylaminomethyl-4-methylpyrrolidine (3.49 g).

MS (EI) m/z: 294 (M$^+$).

HRMS (EI)

Calcd for $C_{20}H_{26}N_2$: 294.2096. Found: 294.2072.

Step 4:

Using (3R,4S)-1-benzyl-3-benzylaminomethyl-4-methylpyrrolidine (3.40 g), the same procedure was followed as in Step 4 of Reference Example 4 to give (3R,4S)-1-benzyl-3-(N-benzyl-N-cyclopropyl)aminomethyl-4-methylpyrrolidine (3.72 g).

MS (FAB$^+$) m/z: 335 (MH$^+$).

HRMS (EI)

Calcd for $C_{23}H_{31}N_2$ (MH$^+$): 335.2487.

Found: 335.2503.

Step 5:

Using (3R,4S)-1-benzyl-3-(N-benzyl-N-cyclopropyl)aminomethyl-4-methylpyrrolidine (3.60 g), the same procedure was followed as in Step 5 of Reference Example 4 to give (3R,4S)-3-cyclopropylaminomethyl-4-methylpyrrolidine (1.29 g).

MS (CI$^+$)m/z: 155 (MH$^+$).

HRMS (CI$^+$)

Calcd for $C_9H_{19}N_2$: 155.1548. Found: 155.1539.

Reference Example 6

Synthesis of (3S,4R)-3-cyclopropylaminomethyl-4-methylpyrrolidine

Step 1:

Using (3S,4R)-1-benzyl-3-hydroxy-4-methylpyrrolidine (4.62 g), the same procedure was followed as in Step 1 of Reference Example 5 to give (3S,4R)-1-benzyl-4-methyl-3-pyrrolidinecarbonitrile (3.07 g).

$^1$H NMR(CDCl$_3$): δ 1.22 (d, J=6.8 Hz, 3H), 2.13 (t, J=9.3 Hz, 1H), 2.45-2.55 (m, 1H), 2.61-2.65 (m, 1H), 2.99 (dd, J=6.8 Hz, 9.3 Hz, 1H), 3.09-3.19 (m, 2H), 3.62 (s, 2H), 7.27-7.34 (m, 5H).

Step 2:

Using (3S,4R)-1-benzyl-4-methyl-3-pyrrolidinecarbonitrile (3.00 g), the same procedure was followed as in Step 2 of Reference Example 4 to give (3R,4R)-1-benzyl-4-methyl-3-aminomethylpyrrolidine (1.44 g).

MS (EI)m/z: 204 (M$^+$).
HRMS (EI)
Calcd for $C_{13}H_{20}N_2$(M$^+$): 204.1626. Found 204.1614.

Step 3:

Using (3R,4R)-1-benzyl-4-methyl-3-aminomethylpyrrolidine (1.06 g), the same procedure was followed as in Step 3 of Reference Example 4 to give (3S,4R)-1-benzyl-3-benzylaminomethyl-4-methylpyrrolidine (1.20 g).

MS (EI) m/z: 294 (M$^+$)
HRMS (EI)
Calcd for $C_{20}H_{26}N_2$: 294.2096. Found: 294.2106.

Step 4:

Using (3S,4R)-1-benzyl-3-benzylaminomethyl-4-methylpyrrolidine (1.40 g), the same procedure was followed as in Step 4 of Reference Example 4 to give (3S,4R)-1-benzyl-3-(N-benzyl-N-cyclopropyl)aminomethyl-4-methylpyrrolidine (1.55 g).

MS (FAB$^+$) m/z: 335 (MH$^+$)
HRMS (EI)
Calcd for $C_{23}H_{31}N_2$: 335.2487.
Found: 335.2498.

Step 5:

Using (3S,4R)-1-benzyl-3-(N-benzyl-N-cyclopropyl)aminomethyl-4-methylpyrrolidine (700 mg), the same procedure was followed as in Step 5 of Reference Example 4 to give (3S,4R)-3-cyclopropylaminomethyl-4-methylpyrrolidine (215 mg).

MS (CI$^+$)m/z: 155 (MH$^+$)
HRMS (CI$^+$)
Calcd for $C_9H_{19}N_2$: 155.1548. Found: 155.1510.

Reference Example 7

Synthesis of trans-3-cyclopropylaminomethyl-4-trifluoromethylpyrrolidine

Step 1:

Using trans-1-benzyl-4-trifluoromethyl-3-pyrrolidine carboxylic acid (3.00 g), the same procedure was followed as in Step 1 of Reference Example 1 to give trans-1-benzyl-4-trifluoromethyl-3-pyrrolidine carboxamide (3.32 g).

$^1$H NMR(CDCl$_3$): δ 0.42-0.46 (m, 2H), 0.75-0.79 (m, 2H), 2.64-2.78 (m, 4H), 2.82-2.86 (m, 1H), 2.95 (t, J=9.3 Hz, 1H), 3.10-3.22 (m,1H), 3.59 (d, J=13.2 Hz, 1H), 3.68 (d, J=12.7 Hz, 1H), 6.34-6.53 (br, 1H), 7.26-7.36 (m, 5H).

Step 2:

Using trans-1-benzyl-4-trifluoromethyl-3-pyrrolidine carboxamide (3.21 g), the same procedure was followed as in Step 2 of Reference Example 1 to give trans-1-benzyl-3-[[(N-tert-butoxycarbonyl-N-cyclopropyl)amino]methyl]-4-trifluoromethylpyrrolidine (3.37 g).

MS (FAB$^+$) m/z: 399 (MH$^+$).
HRMS (FAB$^+$)
Calcd for $C_{21}H_{30}F_3N_2O_2$: 399.2259. Found: 399.2254.

Step 3:

Using trans-1-benzyl-3-[[(N-tert-butoxycarbonyl-N-cyclopropyl)amino]methyl]-4-trifluoromethylpyrrolidine (3.27 g), the same procedure was followed as in Step 3 of Reference Example 1 to give trans-3-[[(N-tert-butoxycarbonyl-N-cyclopropyl)amino]methyl]-4-trifluoromethylpyrrolidine (2.38 g).

MS (FAB$^+$) m/z: 309 (MH$^+$).
HRMS (FAB$^+$)
Calcd for $C_{14}H_{24}F_3N_2O_2$: 309.1790. Found: 309.1783.

Step 4:

Using trans-3-[[(N-tert-butoxycarbonyl-N-cyclopropyl)amino]methyl]-4-trifluoromethylpyrrolidine (2.30 g), the same procedure was followed as in Step 4 of Reference Example 1 to give trans-3-cyclopropylaminomethyl-4-trifluoromethylpyrrolidine (992 mg).

$^1$H NMR(CDCl$_3$): δ 0.29-0.33 (m, 2H), 0.42-0.46 (m, 2H), 2.10-2.15 (m, 1H), 2.30-2.39 (m, 1H), 2.41-2.53 (m, 1H), 2.62-2.71 (m, 2H), 2.83 (dd, J=6.3 Hz, 11.7 Hz, 1H), 3.10 (d, J=6.8 Hz, 2H), 3.18 (dd, J=7.8 Hz, 11.7 Hz, 1H).

Elemental analysis (%)
Calcd for $C_9H_{15}F_3N_2$.2CF$_3$COOH: C, 35.79; H, 3.93; N, 6.42. Found: C, 35.82; H, 3.90; N, 6.59.

Reference Example 8

Synthesis of (3R,4S)-3-cyclopropylaminomethyl-4-fluoropyrrolidine (Process I)

Step 1:

(E)-3-Benzyloxypropenyl-(1R)-camphorsultam (21.6 g) was dissolved in dichloromethane (300 mL) containing trifluoroacetic acid (0.116 mL). To this solution, N-methoxymethyl-N-(trimethylsilyl)benzylamine (15.0 g) was added dropwise at room temperature and the mixture was stirred for 2 hours. Subsequently, the reaction mixture was sequentially washed with a saturated aqueous solution of sodium bicarbonate (2×200 mL) and water (200 mL), dried over anhydrous sodium sulfate, and concentrated under reduced pressure. The resulting pale yellow oily material was dissolved in diethyl ether (150 mL) and the solution was allowed to stand at room temperature for 18 hours. The resulting crystals were filtered, washed with diethyl ether, dried over anhydrous sodium sulfate. This gave N-[[(3S,4R)-benzyl-4-benzyloxypyrrolidin-3-yl]carbonyl]-(2'S)-bornane-10,2-sultam as white crystals (11.5 g). The filtrate and the washings were combined and concentrated under reduced pressure. The residue was then purified by silica gel column chromatography (eluant: cyclohexane: ethyl acetate=4:1) to give additional N-[[(3S,4R)-benzyl-4-benzyloxypyrrolidin-3-yl]carbonyl]-(2'S)-bornane-10,2-sultam (8.48 g).

$^1$H NMR(CDCl$_3$): δ 0.95 (s, 3H), 1.02 (s, 3H), 1.32-1.45 (m, 2H), 1.86-1.96 (m, 3H), 2.00-2.10 (m, 2H), 2.57 (dd, J=9.3 Hz, 5.3 Hz), 2.69 (dd, J=9.8 Hz, 3.9 Hz, 1H), 2.93 (dd, J=10.3 Hz, 6.3 Hz, 1H), 3.20 (t, J=9.3 Hz), 3.42-3.51 (m, 3H), 3.69-3.74 (m, 2H), 3.90 (d, J=11.7 Hz), 4.54 (d, J=11.7 Hz), 4.63-4.66 (m, 1H), 7.22-7.31 (m, 10H).

Step 2:

Lithium aluminum hydride (80%, 5.56 g) was suspended in tetrahydrofuran (170 mL). While the suspension was chilled in a salt-ice bath, N-[[(3S,4R)-benzyl-4-benzyloxypyrrolidin-3-yl]carbonyl]-(2'S)-bornane-10,2-sultam (19.9 g) in tetrahydrofuran (300 mL) was added dropwise and the mixture was stirred for 1 hour at −5° C. or below. Subsequently, water (34 mL) was carefully added dropwise and the insoluble material was filtered and washed with ethyl acetate (2×400 mL). The filtrate and the washings were combined and extracted with 1 mol/L hydrochloric acid (2×500 mL). The hydrochloric acid layers were combined and a 30% aqueous solution of sodium hydroxide was added to make the extract basic (pH 14). The hydrochloric acid extract was then extracted with diethyl ether (2×500 mL). The diethyl ether layers were combined and concentrated under reduced pressure. The resulting residue was purified by silica gel column chromatography (eluate: hexane: ethyl acetate=1:1) to give (3R,4R)-(1-benzyl-4-benzyloxypyrrolidin-3-yl)methanol as a pale yellow oil (9.91 g).

$^1$H NMR(CDCl$_3$): δ 2.29-2.34(m, 1H), 2.40 (dd, J=10.3 Hz, 4.4 Hz, 1H), 2.68 (dd, J=9.3 Hz, 2.4 Hz, 1H), 2.75 (dd, J=9.8 Hz, 6.3 Hz, 1H), 3.18 (dd, J=9.8 Hz, 6.8 Hz, 1H), 3.61 (s, 2H), 3.65 (dd, J=10.3 Hz, 4.4 Hz, 1H), 3.73 (dd, J=10.3 Hz, 4.4 Hz, 1H), 4.07 (ddd, J=6.3 Hz, 4.4 Hz, 2.0 Hz, 1H), 4.48 (s, 2H), 7.25-7.35 (m, 10H).

Step 3:

Process A: (3R,4R)-(1-Benzyl-4-benzyloxypyrrolidin-3-yl)methanol (9.80 g) was dissolved in ethanol (100 mL). To this solution, 10% palladium carbon (2.00 g) was added and the mixture was stirred at 50° C. for 21 hours under a hydrogen pressure of 3.9×10$^5$ Pa. The catalyst in the mixture was filtered through a Celite pad, and the catalyst and the Celite pad were washed with ethanol. The filtrate and the washings were combined and concentrated under reduced pressure. The resulting residue was dissolved in ethanol (100 mL), followed by addition of 10% palladium carbon (2.00 g) and stirring at 50° C. for 20 hours under a hydrogen pressure of 3.9×10$^5$ Pa. Subsequently, the catalyst in the mixture was filtered through a Celite pad, and the catalyst and the Celite pad were washed with ethanol. The filtrate and the washings were combined and concentrated under reduced pressure. The resulting residue was dried under reduced pressure to give (3R,4R)-(4-hydroxypyrrolidin-3-yl)methanol as a pale brown oil (3.77 g).

$^1$H NMR(DMSO-d$_6$): δ 1.96-2.03 (m, 1H), 2.61 (dd, J=11.6 Hz, 5.5 Hz, 1H), 2.68 (dd, J=11.6 Hz, 3.1 Hz, 1H), 2.91 (dd, J=11.1 Hz, 5.5 Hz, 1H), 3.06 (dd, J=11.0 Hz, 7.3 Hz, 1H), 3.26 (dd, J=10.4 Hz, 7.3 Hz, 1H), 3.37 (dd, J=10.4 Hz, 6.1 Hz), 3.90-3.93 (m, 1H).

Sodium hydroxide (2.70 g) was dissolved in water (25 mL) and dioxane (15 mL) was added to the solution. (3R,4R)-(4-Hydroxypyrrolidin-3-yl)methanol (1.00 g) was then dissolved in the solution. While the mixture was chilled in an ice water bath, carbobenzoxy chloride (0.97 mL) was added dropwise. The reaction mixture was stirred at 5° C. or below for 1 hour and a second portion of carbobenzoxy chloride (0.97 mL) was added dropwise, followed by stirring at 5° C. or below for another hour and dropwise addition of a third portion of carbobenzoxy chloride (0.97 mL). The resulting mixture was stirred at 5° C. or below for 1 hour and then at room temperature for 1 hour. Subsequently, the reaction mixture was extracted with dichloromethane (2×100 mL). The dichloromethane layers were combined, dried over anhydrous sodium sulfate, concentrated under reduced pressure. The resulting residue was purified by silica gel column chromatography (eluant: hexane: ethyl acetate=1:1->ethyl acetate: methanol=20:1) to give (3R,4R)-[1-benzyloxycarbonyl-4-hydroxypyrrolidin-3-yl]methanol as a milky white tar-like material (1.18 g).

MS (EI) m/z: 251 (M$^+$).

$^1$H NMR(CDCl$_3$): δ 2.08-2.40 (br +m, 2H), 2.58-2.79 (br, 1H), 3.20 (dd, J=11.0 Hz, 7.3 Hz, 1H), 3.32 (dt, J=11.1 Hz, 5.5 Hz, 1H), 3.59-3.76 (m, 4H), 4.23-4.33 (br, 1H), 5.12 (s, 2H), 7.28-7.36 (m, 5H).

Process B: (3R,4R)-[1-Benzyl-4-benzyloxypyrrolidin-3-yl]methanol (10.0 g) was dissolved in methanol (200 mL). To this solution, 10% palladium carbon (3.00 g) suspended in water (60 mL) was added, followed by ammonium formate (21.2 g). The mixture was then refluxed for 4 hours while being stirred. The catalyst in the reaction mixture was filtered through a Celite pad, and the catalyst and the Celite pad were washed with a mixture of methanol and water (80:20). The filtrate and the washings were combined and were concentrated under reduced pressure. The resulting pale brown tar-like material was dissolved in N,N-dimethylformamide (100 mL). While the solution was chilled in an ice water bath, triethylamine (9.40 mL) was added, followed by dropwise addition of carbobenzoxy chloride (6.00 mL). The mixture was stirred for 1.5 hours in the ice water bath and was subsequently concentrated under reduced pressure. The resulting residue was dissolved in ethyl acetate (400 mL), washed with saturated brine (2×100 mL), dried over anhydrous sodium sulfate, and concentrated under reduced pressure. The residue was purified by silica gel column chromatography (eluant: ethyl acetate->ethyl acetate: methanol=20:1) to give (3R, 4R)-[1-benzyloxycarbonyl-4-hydroxypyrrolidin-3-yl] methanol as a milky white tar-like product (7.66 g).

This compound was identical to the compound obtained by Process A.

Step 4:

Process A: (3R,4R)-(1-Benzyloxycarbonyl-4-hydroxypyrrolidin-3-yl)methanol (3.19 g) was dissolved in N,N-dimethylformamide (91 mL). While this solution was chilled in an ice water bath, imidazole (6.05 g) and then tert-butylchlorodimethylsilane (5.74 g) were added. The reaction mixture was stirred at room temperature for 3 hours and was concentrated under reduced pressure. The residue was then dissolved in diethyl ether (400 mL). The diethyl ether layer was washed with saturated brine (2×100 mL), dried over anhydrous sodium sulfate, and concentrated under reduced pressure. The resulting residue was purified on silica gel column chromatography (eluant: hexane: ethyl acetate=4:1) to give (3R, 4R)-1-benzyloxycarbonyl-3-(tert-butyldimethylsilyl)oxymethyl-4-(tert-butyldimethylsilyl)oxypyrrolidine as a colorless oil (5.46 g).

MS (CI$^+$) m/z: 480(MH$^+$).

$^1$H NMR(CDCl$_3$): δ 0.03 (s, 3H), 0.05 (s, 3H), 0.06 (s, 3H), 0.07 (s, 3H), 0.87 (s, 9H), 0.88 (s, 9H), 2.17-2.27 (m, 1H), 3.21-3.28 (m, 2H), 3.48-3.67 (m, 4H), 4.21-4.28 (m, 1H), 5.13 (s, 2H), 7.31-7.37 (m, 5H).

(3R,4R)-1-Benzyloxycarbonyl-3-(tert-butyldimethylsilyl)oxymethyl-4-(tert-butyldimethylsilyl)oxypyrrolidine (5.46 g) was dissolved in tetrahydrofuran (23 mL). While this solution was chilled in an ice water bath, water (23 mL) and acetic acid (68 mL) were sequentially added and the mixture was stirred at room temperature for 8 hours. The reaction mixture was concentrated under reduced pressure and the residue was purified by silica gel column chromatography (eluant: hexane: ethyl acetate=4:1->1:1) to give (3R,4R)-1-benzyloxycarbonyl-3-hydroxymethyl-4-(tert-butyldimethylsilyloxy)pyrrolidine as a colorless oil (2.74 g).

MS (CI$^+$) m/z: 366(MH$^+$).

$^1$H NMR(CDCl$_3$): δ 0.07-0.08 (m, 6H), 0.88 (s, 9H), 2.23-2.35 (m, 1H), 3.21-3.30 (m, 2H), 3.58-3.72 (m, 4H), 4.17-4.25 (m, 1H), 5.128 (s, 1H), 5.135(s, 1H), 7.31-7.37 (m, 5H).

(3R,4R)-1-Benzyloxycarbonyl-3-hydroxymethyl-4-(tert-butyldimethylsilyloxy)pyrrolidine (2.73 g) was dissolved in dichloromethane (60 mL). While this solution was chilled in an ice water bath, triethylamine (1.21 mL) was added, followed by dropwise addition of methanesulfonyl chloride (0.71 mL) at −5° C. or below. The mixture was stirred for 1 hour at −5° C. or below and was then washed with water (2×25 mL), dried over anhydrous sodium sulfate, and concentrated under reduced pressure. The resulting residue was dissolved in N,N-dimethylformamide (60 mL), followed by addition of sodium azide (1.14 g) and stirring at 100° C. for 2 hours. The reaction mixture was then concentrated under reduced pressure. Water (30 mL) was added and the mixture was extracted with diethyl ether (2×100 mL). The diethyl ether layers were combined, dried over anhydrous sodium sulfate, and concentrated under reduced pressure. The resulting residue was purified by silica gel column chromatography (eluant: hexane: ethyl acetate=4:1) to give (3R,4R)-3-azidomethyl-1-benzyloxycarbonyl-4-(tert-butyldimethylsilyl) oxypyrrolidine as a colorless oil (3.06 g).

MS (CI$^+$) m/z: 391 (MH$^+$).

$^1$H NMR(CDCl$_3$): δ 0.07-0.09 (m, 3H), 2.23-2.34 (m, 1H), 3.19-3.25 (m, 2H), 3.27-3.40 (m, 2H), 3.60-3.71 (m, 2H), 4.11-4.17 (m, 1H), 5.13 (s, 2H), 7.31-7.37 (m, 5H).

(3R,4R)-3-Azidomethyl-1-benzyloxycarbonyl-4-- (tert-butyldimethylsilyl)oxypyrrolidine (3.05 g) was dissolved in tetrahydrofuran (50 mL). While this solution was chilled in an ice water bath, tetrabutylammonium fluoride (1 mol/L tetrahydrofuran solution, 13.3 mL) was added dropwise and the mixture was stirred for 1 hour, followed by addition of saturated brine (70 mL) and the mixture was extracted with ethyl acetate (150 mL, 100 mL). The ethyl acetate layers were combined, dried over anhydrous sodium sulfate, and concentrated under reduced pressure. The resulting residue was purified by silica gel column chromatography (eluant: ethyl acetate) to give (3R,4R)-3-azidomethyl-1-benzyloxycarbonyl-4-hydroxypyrrolidine as a milky white syrup (2.01 g).

MS (CI$^+$)m/z: 277 (MH$^+$).

$^1$H NMR (CDCl$_3$): δ 2.18-2.30 (br, 1H), 2.32-2.40 (m, 1H), 3.24 (dd, J=11.6 Hz, 6.1 Hz, 1H), 3.30-3.47 (m, 3H), 3.68-3.75 (m, 2H), 4.18-4.24 (m, 1H), 5.13 (s, 2H), 7.31-7.37 (m, 5H).

Process B: (3R,4R)-[1-Benzyloxycarbonyl-4-hydroxypyrrolidin-3-yl]methanol (3.00 g), sodium azide (2.32 g), triphenylphosphine (3.43 g) and N,N-dimethylformamide (60 mL) were mixed together. While this mixture was chilled in an ice water bath, carbon tetrabromide (4.34 g) in dichloromethane (14 mL) was added dropwise. The reaction mixture was stirred at room temperature for 25 hours and then at 60° C. for 2 hours. Subsequently, methanol (5 mL) was added and the mixture was concentrated under reduced pressure. The resulting residue was dissolved in ethyl acetate (200 mL) and the solution was washed with saturated brine (2×50 mL), dried over anhydrous sodium sulfate, and concentrated under reduced pressure. The resulting residue was purified by silica gel column chromatography (eluant: ethyl acetate:hexane=2: 1) to give (3R,4R)-3-azidomethyl-1-benzyloxycarbonyl-4-hydroxypyrrolidine as a pale brown syrup (2.94 g).

This compound was identical to the compound obtained in Process A.

Process C: (3R,4R)-[1-Benzyloxycarbonyl-4-hydroxypyrrolidin-3-yl]methanol (150 mg) was dissolved in dichloromethane (12 mL) and 2,4,6-collidine (0.79 mL) was added to the solution. While this mixture was chilled in an ice water bath, methanesulfonyl chloride (46.2 µL) was added dropwise. The mixture was stirred for 2 hours in the ice water bath and was stored in a refrigerator (3° C.) for 15 hours. Subsequently, the reaction mixture was washed sequentially with water (2 mL), 1 mol/L hydrochloric acid (2×2 mL) and saturated brine (2×2 mL), dried over anhydrous sodium sulfate, and concentrated under reduced pressure. The resulting residue was purified by silica gel column chromatography (eluant: hexane: ethyl acetate 1:2->ethyl acetate) to give 38.7 mg of (3R,4R)-1-benzyloxycarbonyl-3-methanesulfonyloxy-4-methanesulfonyloxymethylpyrrolidine as a pale yellow syrup and (3R,4R)-1-benzyloxycarbonyl-3-hydroxy-4-methanesulfonyloxymethylpyrrolidine (133 mg) as a white syrup.

(3R,4R)-1-Benzyloxycarbonyl-3-hydroxy-4-methanesulfonyloxymethylpyrrolidine (125 mg) was then dissolved in N,N-dimethylformamide (3 mL) and sodium azide (50.0 mg) was added. The mixture was stirred at 100° C. for 1 hour and was concentrated under reduced pressure. The resulting residue was dissolved in ethyl acetate (5 mL). The solution was then washed with water (2×1 mL), dried over anhydrous sodium sulfate, and concentrated under reduced pressure. The residue was purified by silica gel column chromatography (eluant: ethyl acetate) to give (3R,4R)-3-azidomethyl-1-benzyloxycarbonyl-4-hydroxypyrrolidine as a milky white syrup (91.0 mg). This compound was identical to the compound obtained by Process A.

Step 5:

Process A: (3R,4R)-3-Azidomethyl-1-benzyloxycarbonyl-4-hydroxypyrrolidine (1.20 g) was dissolved in dichloromethane (40 mL). While this solution was chilled in a salt/ice bath, diethylaminosulfur trifluoride (1.20 mL) was added dropwise and the mixture was stirred at room temperature for 3 hours. The reaction vessel was again chilled in a salt/ice bath, followed by dropwise addition of a second portion of diethylaminosulfur trifluoride (0.57 mL) and stirring at room temperature for 2 hours. While the reaction mixture was kept chilled in the ice bath, a saturated aqueous solution of sodium bicarbonate (40 mL) was added dropwise and the dichloromethane layer was separated. The dichloromethane layer was then washed with a saturated aqueous solution of sodium bicarbonate (2×20 mL) and then water (20 mL), dried over anhydrous sodium sulfate, and concentrated under reduced pressure. The resulting residue was purified by silica gel column chromatography (eluant: hexane: ethyl acetate=2: 1) to give (3R,4S)-3-azidomethyl-1-benzyloxycarbonyl-4-fluoropyrrolidine as a pale brown oil (726 mg).

MS (CI$^+$) m/z: 279 (MH$^+$).

$^1$H NMR(CDCl$_3$): δ 2.34-2.54 (m, 1H), 3.22 (dt, J=11.0 Hz, 2.4 Hz, 1H), 3.39-3.49 (m, 1H), 3.54-3.69 (m, 2H), 3.73-3.91 (m, 2H), 5.14 (s, 2H), 5.16 (dt, J=53.2 Hz, 3.7 Hz, 1H), 7.32-7.37 (m, 5H).

Process B: (3R,4R)-3-Azidomethyl-1-benzyloxycarbonyl-4-hydroxypyrrolidine (1.79 g) was dissolved in toluene (56 mL). While this solution was chilled in an ice water bath, 1,8-diazabicyclo[5.4.0]undec-7-ene (2.03 mL) was added, followed by dropwise addition of perfluoro-1-octanesulfonyl fluoride (2.80 mL) and stirring for 1 hour. The insoluble material in the reaction mixture was filtered and washed with toluene. The filtrate and the washings were combined and concentrated under reduced pressure. The resulting residue was purified by silica gel column chromatography (eluant: hexane: ethyl acetate=2:1) to give (3R,4S)-3-azidomethyl-1-benzyloxycarbonyl-4-fluoropyrrolidine as a pale brown syrup (1.58 g). This compound was identical to the compound obtained by Process A.

Step 6:

(3R,4S)-3-Azidomethyl-1-benzyloxycarbonyl-4-fluoropyrrolidine (1.35 g) was dissolved in ethanol (30 mL) and platinum (IV) oxide (190 mg) was added. The mixture was then stirred at room temperature for 2 hours under a stream of hydrogen gas (blown by a balloon). The catalyst in the reaction mixture was filtered through a Celite pad, and the catalyst and the Celite pad were washed with ethanol. The filtrate and the washings were then combined and concentrated under reduced pressure. The resulting residue was purified by silica gel column chromatography (eluant: ethyl acetate: methanol=10:1) to give (3S,4S)-3-aminomethyl-1-benzyloxycarbonyl-4-fluoropyrrolidine as a pale brown oil (1.13 g).

MS (CI$^+$) m/z: 253(MH$^+$).

Step 7:

(3S,4S)-3-Aminomethyl-1-benzyloxycarbonyl-4-fluoropyrrolidine (1.10 g) was dissolved in methanol (13 mL). To this solution, molecular sieve 4A (440 mg) and then benzaldehyde (0.44 mL) were added. The mixture was stirred at room temperature for 1 hour, followed by addition of a borane/pyridine complex (0.44 mL) and further stirring at room temperature for 3.5 hours. Subsequently, 6 mol/L hydrochloric acid (7.3 mL) was added and the mixture was stirred at room temperature for 1 hour. A 30% aqueous solution of sodium hydroxide was then added to make the mixture basic. The mixture was extracted with diethyl ether (2×100 mL). The diethyl ether layers were combined, dried over anhydrous sodium sulfate, and concentrated under reduced pressure. The resulting residue was purified by silica gel column chromatography (eluant: hexane: ethyl acetate=4:1->1:1) to give (3S,4S)-3-benzylaminomethyl-1-benzyloxycarbonyl-4-fluoropyrrolidine as a colorless tar (1.18 g).

MS (CI$^+$) m/z: 343 (MH$^+$).

Step 8:

(3S,4S)-3-Benzylaminomethyl-1-benzyloxycarbonyl-4-fluoropyrrolidine (1.15 g) was dissolved in methanol (21 mL). To this solution, molecular sieves 3A (1.05 g), acetic acid (1.92 mL), [(1-ethoxycyclopropyl)oxy]trimethylsilane (2.70 mL) and sodium cyanoborohydride (633 mg) were added and the mixture was refluxed for 2 hours while being stirred. The insoluble material in the reaction mixture was filtered through a Celite pad. The collected insoluble material and the Celite pad were washed with methanol. The filtrate and the washings were combined and a 2 mol/L aqueous solution of sodium hydroxide was added to make the solution basic (pH 14). Methanol was then evaporated under reduced pressure and the residue was extracted with diethyl ether (2×100 mL). The diethyl ether layers were combined, dried over anhydrous sodium sulfate, and concentrated under reduced pressure. The resulting residue was purified by silica gel column chromatography (eluant: hexane: ethyl acetate=4:1) to give (3S,4S)-3-(N-benzyl-N-cyclopropyl)aminomethyl-1-benzyloxycarbonyl-4-fluoropyrrolidine as a colorless tar (1.26 g).

MS (EI) m/z: 382 (M$^+$)

Step 9:

(3S,4S)-3-(N-Benzyl-N-cyclopropyl)aminomethyl-1-benzyloxycarbonyl-4-fluoropyrrolidine (1.22 g) was dissolved in ethanol (14 mL). To this solution, 10% palladium carbon (150 mg) was added and the mixture was stirred at room temperature for 4 hours under a stream of hydrogen gas (blown by a balloon). The catalyst in the reaction mixture was filtered through a Celite pad, and the catalyst and the Celite pad were washed with ethanol. The filtrate and the washings were then combined and concentrated under reduced pressure. The resulting residue was purified by silica gel column chromatography (eluant: ethyl acetate: methanol=20:1). The eluate was distilled under reduced pressure to give (3R,4S)-3-cyclopropylaminomethyl-4-fluoropyrrolidine (414 mg) as a colorless oil.

MS (CI$^+$) m/z: 159 (MH$^+$).
HRMS (CI$^+$)
Calcd for $C_8H_{16}FN_2$: 159.1298. Found: 159.1316.

Reference Example 9

Synthesis of (3R,4S)-3-cyclopropylaminomethyl-4-fluoropyrrolidine (Process II)

Step I:

(3R,4R)-(4-Hydroxypyrrolidin-3-yl)methanol (1.18 g) was dissolved in ethanol (25 mL). To this solution, triethylamine (1.40 mL) was added and while the mixture was chilled in a salt/ice water bath, benzyl bromide (1.10 mL) was added dropwise. The mixture was stirred at room temperature for 1 hour and was concentrated under reduced pressure. The resulting residue was purified by silica gel column chromatography (eluant: ethyl acetate: methanol=20:1) to give (3R, 4R)-(1-benzyl-4-hydroxypyrrolidin-3-yl)methanol as a milky white syrup (1.02 g).

MS (EI$^+$) m/z: 207 (M$^+$).
HRMS (EI$^+$)
Calcd for $C_{12}H_{17}NO_2$: 207.1259. Found: 207.1237.

Step 2:

(3R,4R)-(1-Benzyl-4-hydroxypyrrolidin-3-yl)methanol (1.36 g) was dissolved dichloromethane (14 mL). While this solution was chilled in a dry ice/acetone bath, triethylamine (0.83 mL) was added, followed by dropwise addition of methanesulfonyl chloride (0.46 mL) and stirring for 30 min. Water (10 mL) was added and the reaction mixture was allowed to warm to room temperature and was diluted with dichloromethane (20 mL). The dichloromethane layer was separated, washed with water (2×10 mL), dried over anhydrous sodium sulfate, and concentrated under reduced pressure. The resulting residue was purified by silica gel column chromatography (hexane: ethyl acetate=1:1->ethyl acetate: methanol=20:1). The fraction eluted with hexane/ethyl acetate (1:1) yielded (3R,4R)-1-benzyl-3-methanesulfonyloxy-4-methanesulfonyloxymethylpyrrolidine as a milky white syrup (585 mg).

MS (EI$^+$) m/z: 363 (M$^+$).
HRMS (EI$^+$)
Calcd for $C_{14}H_{21}NO_6S_2$: 363.0810. Found: 363.0804.

The fraction eluted with ethyl acetate/methanol (20:1) yielded (3R,4R)-1-benzyl-3-hydroxy-4-methanesulfonyloxymethylpyrrolidine as white crystals (840 mg)

MS (EI$^+$) m/z: 285 (M$^+$).
HRMS (EI$^+$)
Calcd for $C_{13}H_{19}NO_4S$: 285.1035
Found: 285.1045.

Step 3:

(3R,4R)-1-Benzyl-3-hydroxy-4-methanesulfonyloxymethylpyrrolidine (835 mg), sodium azide (381 mg) and N,N-dimethylformamide (12 mL) were mixed together, and the mixture was stirred at 120° C. for 1 hour and was concentrated under reduced pressure. Water (10 mL) was then added to the resulting residue and the mixture was extracted with diethyl ether (2×30 mL). The diethyl ether layers were combined, dried over anhydrous sodium sulfate, and concentrated under reduced pressure. The resulting residue was purified by silica gel column chromatography (eluant: ethyl acetate: methanol=20:1) to give (3R,4R)-3-azidomethyl-1-benzyl-4-hydroxypyrrolidine as a pale brown oil (576 mg).

MS (EI$^+$) m/z: 232 (M$^+$).
HRMS (EI$^+$)
Calcd for $C_{12}H_{16}N_4O$: 232.1324. Found: 232.1309.

Step 4:

(3R,4R)-3-Azidomethyl-1-benzyl-4-hydroxypyrrolidine (566 mg) was dissolved in dichloromethane (9 mL). While this solution was chilled in an ice water bath, diethylaminosulfur trifluoride (0.39 mL) was added dropwise and the mixture was stirred at room temperature for 2 hours. While the reaction vessel was chilled in an ice water bath, a saturated aqueous solution of sodium bicarbonate (9 mL) was added and the mixture was diluted with dichloromethane (15 mL). The dichloromethane layer was separated, washed sequentially with a saturated aqueous solution of sodium bicarbonate (10 mL) and water (10 mL), dried over anhydrous sodium sulfate, and concentrated under reduced pressure. The resulting residue was purified by silica gel column chromatography (eluant: hexane: ethyl acetate=4:1). The first half fraction yielded (3R,4R)-3-azidomethyl-1-benzyl-4-fluoropyrrolidine as a pale brown oil (76.7 mg).

MS (EI$^+$) m/z: 234 (M$^+$).

HRMS (EI$^+$)

Calcd for $C_{12}H_{15}FN_4$: 234.1281. Found: 234.1263.

The second half fraction yielded (3R,4S)-3-azidomethyl-1-benzyl-4-fluoropyrrolidine as a pale brown oil (220 mg).

MS (EI$^+$) m/z: 234 (M$^+$).

HRMS (EI$^+$)

Calcd for $C_{12}H_{15}FN_4$: 234.1281. Found: 234.1269.

Step 5:

(3R,4S)-3-Azidomethyl-1-benzyl-4-fluoropyrrolidine (215 mg) was dissolved in ethanol (3 mL) and platinum (IV) oxide (30.0 mg) was added. The mixture was stirred at room temperature for 5 hours under a stream of hydrogen gas (blown by a balloon). The catalyst in the reaction mixture was filtered through a Celite pad, and the catalyst and the Celite pad were washed with ethanol. The filtrate and the washings were then combined and concentrated under reduced pressure to give (3S,4S)-3-aminomethyl-1-benzyl-4-fluoropyrrolidine as a pale brown oil (191 mg).

MS (CI$^+$) m/z: 209 (MH$^+$).

HRMS (CI$^+$)

Calcd for $C_{12}H_{18}FN_2$: 209.1454. Found: 209.1465.

Step 6:

(3S,4S)-3-Aminomethyl-1-benzyl-4-fluoropyrrolidine (186 mg) was dissolved in methanol (4 mL). To this solution, molecular sieves 4A (80.0 mg) and then benzaldehyde (90.8 µL) were added. The mixture was stirred at room temperature for 1 hour, followed by addition of a borane/pyridine complex (90.2 µL) and further stirring at room temperature for 3 hours. Subsequently, 6 mol/L hydrochloric acid (1.5 mL) was added and the mixture was stirred for 1 hour. A 6 mol/L aqueous solution of sodium hydroxide was then added to make the mixture basic. The mixture was extracted with diethyl ether (3×10 mL). The diethyl ether layers were combined, dried over anhydrous sodium sulfate, and concentrated under reduced pressure. The resulting residue was purified by silica gel column chromatography (eluant: hexane: ethyl acetate=4:1) to give (3S,4S)-1-benzyl-3-benzylaminomethyl-4-fluoropyrrolidine as a pale brown oil (179 mg).

MS (CI$^+$) m/z: 299 (MH$^+$).

HRMS (CI$^+$)

Calcd for $C_{19}H_{24}FN_2$: 299.1924. Found: 299.1960.

Step 7:

(3S,4S)-1-Benzyl-3-benzylaminomethyl-4-fluoropyrrolidine (175 mg) was dissolved in methanol (2 mL). To this solution, molecular sieves 3A (180 mg), acetic acid (0.36 mL), [(1-ethoxycyclopropyl)oxy]trimethylsilane (0.47 mL) and sodium cyanoborohydride (110 mg) were added and the mixture was refluxed for 3 hours while being stirred. The insoluble material in the reaction mixture was filtered through a Celite pad. The collected insoluble material and the Celite pad were washed with methanol. The filtrate and the washings were combined and a 2 mol/L aqueous solution of sodium hydroxide was added to make the solution basic (pH 14). Methanol was then evaporated under reduced pressure and the residue was extracted with diethyl ether (3×10 mL). The diethyl ether layers were combined, dried over anhydrous sodium sulfate, and concentrated under reduced pressure. The resulting residue was purified by silica gel column chromatography (eluant: hexane: ethyl acetate=4:1) to give (3R, 4S)-3-(N-benzyl-N-cyclopropyl)aminomethyl-1-benzyl-4-fluoropyrrolidine as a colorless tar (172 mg).

MS (CI$^+$) m/z: 339 (MH$^+$).

HRMS (CI$^+$)

Calcd for $C_{22}H_{28}FN_2$: 339.2237.

Found: 339.2285.

Step 8:

(3R,4S)-3-(N-Benzyl-N-cyclopropyl)aminomethyl-1-benzyl-4-fluoropyrrolidine (170 mg) was dissolved in ethanol (10 mL). To this solution, 10% palladium carbon (200 mg) and chloroform (0.17 mL) were added and the mixture was stirred at 50° C. for 23 hours under a hydrogen pressure of $3.0×10^5$ Pa. The palladium carbon in the reaction mixture was filtered through a Celite pad and was washed, along with the Celite pad, with ethanol. The filtrate and the washings were then combined and concentrated under reduced pressure. To the resulting residue, a 30% aqueous solution of sodium hydroxide (approx. 1 mL) was added to saturation. The mixture was then extracted with diethyl ether (3×10 ml). The diethyl ether layers were combined, dried over anhydrous sodium sulfate, and concentrated under reduced pressure to give (3R,4S)-3-cyclopropylaminomethyl-4-fluoropyrrolidine as a pale brown oil (65.4 mg). This product was identical to the compound obtained in Reference Example 8 (Process I).

Reference Example 10

Synthesis of (3R,4R)-3-cyclopropylaminomethyl-4-fluoropyrrolidine

Step 1:

(3R,4R)-[1-Benzyloxycarbonyl-4-hydroxypyrrolidin-3-yl]methanol (2.50 g), triphenylphosphine (5.74 g) and benzoic acid (2.55 g) were dissolved in tetrahydrofuran (60 mL). While this solution was chilled in a salt/ice bath, diethyl azodicarboxylate (40% toluene solution, 9.53 mL) was added dropwise. The mixture was stirred at 0° C. or below for 1 hour and then at room temperature for 2 hours and was subsequently concentrated under reduced pressure. The resulting residue was purified by silica gel column chromatography (eluant: hexane: ethyl acetate=2:1). The eluted pale brown tar-like material was dissolved in ethanol (60 mL). To this solution, potassium carbonate (4.07 g) in water (30 mL) was added and the mixture was refluxed for 3 hours while being stirred. Subsequently, the reaction mixture was concentrated under reduced pressure and the residue was dissolved in dichloromethane (200 mL). This solution was washed with saturated brine (2×50 mL), dried over anhydrous sodium sulfate, and concentrated under reduced pressure. The resulting residue was purified by silica gel column chromatography (eluant: ethyl acetate: methanol=10:1) to give (3R,4S)-[1-benzyloxycarbonyl-4-hydroxypyrrolidin-3-yl]methanol as a milky white syrup (2.04 g).

MS (EI) m/z: 251 (M$^+$).

Step 2:

(3R,4S)-[1-Benzyloxycarbonyl-4-hydroxypyrrolidin-3-yl]methanol (2.33 g), sodium azide (1.81 g), triphenylphosphine (2.67 g) and N,N-dimethylformamide (46 mL) were mixed together. While the mixture was chilled in an ice water bath, carbon tetrabromide (3.38 g) in dichloromethane (10 mL) was added dropwise. The reaction mixture was stirred at room temperature for 13 hours and then at 60° C. for 3 hours. Subsequently, methanol (3 mL) was added and the mixture was concentrated under reduced pressure. The resulting residue was dissolved in ethyl acetate (200 mL) and the solution was washed with saturated brine (2×50 mL), dried over anhydrous sodium sulfate, and concentrated under reduced pressure. The resulting residue was purified by silica gel column chromatography (eluant: ethyl acetate: hexane=2:1) to give (3R,4S)-3-azidomethyl-1-benzyloxycarbonyl-4-hydroxypyrrolidine as a milky white syrup (2.18 g).

MS (FAB$^+$) m/z: 277 (MH$^+$).

Step 3:

(3R,4S)-3-Azidomethyl-1-benzyloxycarbonyl-4-hydroxypyrrolidine (300 mg) was dissolved in dichloromethane (6 mL). While this solution was chilled in a salt/ice bath, diethylaminosulfur trifluoride (0.43 mL) was added dropwise and the mixture was stirred at room temperature for 4 hours. The reaction vessel was chilled in an ice water bath and a saturated aqueous solution of sodium bicarbonate (6 mL) was added. The dichloromethane layer was then separated, washed with saturated brine (2×2 mL), dried over anhydrous sodium sulfate, and concentrated under reduced pressure. The resulting residue was purified by silica gel column chromatography (eluant: hexane: ethyl acetate=2:1) to give a mixture of (3R,4R)-3-azidomethyl-1-benzyloxycarbonyl-4-fluoropyrrolidine and 3-azidomethyl-1-benzyloxycarbonyl-3-pyrroline (211 mg).

Step 4:

Platinum (IV) oxide (50.0 mg) was suspended in ethanol (7 mL) and the suspension was stirred at room temperature under a stream of hydrogen gas (blown by a balloon) for 30 min. Subsequently, a mixture (551 mg) of (3R,4R)-3-azidomethyl-1-benzyloxycarbonyl-4-fluoropyrrolidine and 3-azidomethyl-1-benzyloxycarbonyl-3-pyrroline in ethanol (3 mL) was added and the mixture was stirred at room temperature under a stream of hydrogen gas (blown by a balloon) for 5 hours. The catalyst in the reaction mixture was filtered and was washed with ethanol. The filtrate and the washings were combined and concentrated under reduced pressure. The resulting residue was purified by silica gel column chromatography (eluant: ethyl acetate->ethyl acetate: methanol=10:1) to give a mixture (313 mg) of (3S,4R)-3-aminomethyl-1-benzyloxycarbonyl-4-fluoropyrrolidine and 3-aminomethyl-1-benzyloxycarbonyl-3-pyrroline.

Step 5:

The mixture (310 mg) of (3S,4R)-3-aminomethyl-1-benzyloxycarbonyl-4-fluoropyrrolidine and 3-aminomethyl-1-benzyloxycarbonyl-3-pyrroline was dissolved in methanol (4 mL). To this solution, molecular sieves 4A (130 mg) and then benzaldehyde (0.13 mL) were added and the mixture was stirred at room temperature for 1 hour. Subsequently, a borane/pyridine complex (0.19 mL) was added and the reaction mixture was further stirred at room temperature for 4 hours. 6 mol/L hydrochloric acid (2 mL) was then added and the mixture was stirred at room temperature for 1 hour, followed by addition of a 30% aqueous solution of sodium hydroxide to make the mixture basic. The mixture was then extracted with diethyl ether (3×10 mL). The diethyl ether layers were combined and concentrated under reduced pressure. The resulting residue was purified by silica gel column chromatography (eluant: dichloromethane: methanol=10:1) to give (3S,4R)-3-benzylaminomethyl-1-benzyloxycarbonyl-4-fluoropyrrolidine as a pale yellow oil (177 mg).

MS (FAB$^+$) m/z: 343 (MH$^+$).
HRMS (FAB$^+$)
Calcd for $C_{20}H_{24}FN_2O_2$: 343.1822. Found: 343.1815.

Step 6:

(3S,4R)-3-Benzylaminomethyl-1-benzyloxycarbonyl-4-fluoropyrrolidine (170 mg) was dissolved in methanol (5 mL). To this solution, molecular sieves 3A (160 mg), acetic acid (0.29 mL), [(1-ethoxycyclopropyl)oxy]trimethylsilane (0.40 mL) and sodium cyanoborohydride (93.5 mg) were added and the mixture was refluxed for 3 hours while being stirred. The insoluble material in the reaction mixture was filtered through a Celite pad. The collected insoluble material and the Celite pad were washed with methanol. The filtrate and the washings were combined and a 2 mol/L aqueous solution of sodium hydroxide was added to make the solution basic (pH>12). Methanol was then evaporated under reduced pressure and the residue was extracted with diethyl ether (3×10 mL). The diethyl ether layers were combined, dried over anhydrous sodium sulfate, and concentrated under reduced pressure. The resulting residue was purified by silica gel column chromatography (eluant: hexane: ethyl acetate=2:1) to give (3S,4R)-3-(N-benzyl-N-cyclopropyl)aminomethyl-1-benzyloxycarbonyl-4-fluoropyrrolidine as a colorless tar (166 mg).

MS (FAB$^+$) m/z: 383 (MH$^+$).
HRMS (FAB$^+$)
Calcd for $C_{23}H_{28}FN_2O_2$: 383.2135. Found: 383.2119.

Step 7:

(3S,4R)-3-(N-Benzyl-N-cyclopropyl)aminomethyl-1-benzyloxycarbonyl-4-fluoropyrrolidine (160 mg) was dissolved in ethanol (3 mL). To this solution, 10% palladium carbon (20.0 mg) was added and the mixture was stirred at room temperature under a stream of hydrogen gas (blown by a balloon) for 5 hours. The catalyst in the reaction mixture was filtered through a Celite pad and the catalyst and the Celite pad were washed with ethanol. The filtrate and the washings were combined and concentrated under reduced pressure. The resulting residue was purified by silica gel column chromatography (eluant: ethyl acetate: methanol=20:1->dichloromethane: methanol=10:1) to give (3R,4R)-3-cyclopropylaminomethyl-4-fluoropyrrolidine as a colorless oil (50.7 mg).

MS (FAB$^+$) m/z: 159 (MH$^+$).
HRMS (FAB$^+$)
Calcd for $C_8H_{16}FN_2$: 159.1298. Found: 159.1286.

Reference Example 11

Synthesis of (3R,4S)-3-[(N-tert-butoxycarbonyl-N-cyclopropyl)amino]methyl-4-fluoromethylpyrrolidine Step 1:

(1S,5R)-7-[(1R)-1-Phenylethyl]-3-oxa-7-azabicyclo[3.3.0]octane-2-one (7.73 g, 33.4 mmol) was dissolved in ethanol (92 mL). To this solution, cyclopropylamine (46.3 ml) was added and the mixture was stirred at 80° C. for 44 hours and was concentrated under reduced pressure. The residue was dissolved in ethyl acetate (300 mL), washed with water (2×50 mL), dried over anhydrous sodium sulfate, and concentrated under reduced pressure. Diisopropylether (300 mL) was added to the residue and the solution was heated to form crystals. The solution was concentrated to approximately half the original volume and the crystals formed were filtered. The collected crystals were washed with diisopropyl ether and were dried under reduced pressure to give (3R,4S)-N-cyclopropyl-4-hydroxymethyl-1-[(1S)-1-phenylethyl]pyrrolidine-3-carboxamide as white crystals (4.41 g). The filtrate and the washings were then combined and concentrated under reduced pressure. The resulting residue was purified by silica gel column chromatography (eluant: hexane: ethyl acetate=1:1->ethyl acetate) to give additional (3R,4S)-N-cyclopropyl-4-hydroxymethyl-1-[(1S)-1-phenylethyl]pyrrolidine-3-carboxamide (1.50 g).

MS (EI) m/z: 288 (M+).

elemental analysis (%)

Calcd for $C_{17}H_{24}N_2O_2 \cdot 0.2H_2O$: C, 69.93; H, 8.42; N, 9.59. Found: C, 70.16; H, 8.32; N, 9.60.

Step 2:

(3R,4S)-N-Cyclopropyl-4-hydroxymethyl-1-[(1S)-1-phenylethyl]pyrrolidine-3-carboxamide (7.54 g) was dissolved in N,N-dimethylformamide (180 mL). While this solution was chilled in an ice water bath, imidazole (2.67 g) and then tert-butylchlorodimethylsilane (4.72 g) were added. The mixture was stirred at room temperature for 90 min and was subsequently concentrated under reduced pressure. The residue was dissolved in ethyl acetate (300 mL), washed with water (2×100 mL), dried over anhydrous sodium sulfate, and concentrated under reduced pressure. The resulting residue was purified by silica gel column chromatography (eluant: ethyl acetate) to give (3R,4S)-N-cyclopropyl-4-(tert-butyldimethylsilyl)oxymethyl-1-[(1S)-1-phenylethyl]pyrrolidine-3-carboxamide as a pale yellow tar (7.05 g).

MS (EI) m/z: 402 (M+).

Step 3:

(3R,4S)-N-Cyclopropyl-4-(tert-butyldimethylsilyl)oxymethyl-1-[(1S)-1-phenylethyl]pyrrolidine-3-carboxamide (7.00 g) was dissolved in toluene (70 mL). A borane/dimethyl sulfide complex (2.20 mL) was added and the mixture was refluxed for 5 hours while being stirred. Subsequently, the reaction was allowed to cool to room temperature, followed by addition of a 10% aqueous solution of sodium carbonate (42 mL) and stirring at 100° C. for 1 hour. The toluene layer was separated, washed with water (2×30 mL), dried over anhydrous sodium sulfate, and concentrated under reduced pressure. The resulting residue was purified by silica gel column chromatography (eluant: hexane: ethyl acetate=4:1) to give (3S,4S)-4-(tert-butyldimethylsilyl)oxymethyl-3-cyclopropylaminomethyl-1-[(1S)-1-phenylethyl]pyrrolidine as a colorless oil (4.78 g).

Step 4:

(3S,4S)-4-(tert-Butyldimethylsilyl)oxymethyl-3-cyclopropylaminomethyl-1-[(1S)-1-phenylethyl]pyrrolidine (4.70 g) was dissolved in dichloromethane (70 mL). To this solution, di-tert-butyldicarbonate (2.77 g) was added and the mixture was stirred at room temperature for 2 hours. Subsequently, the reaction mixture was concentrated under reduced pressure and the resulting residue was purified by silica gel column chromatography (eluant: hexane: ethyl acetate=4:1->1:1) to give (3R,4S)-3-[(N-tert-butoxycarbonyl-N-cyclopropyl)amino]methyl-4-(tert-butyldimethylsilyl)oxymethyl-1-[(1S)-1-phenylethyl]pyrrolidine as a colorless oil (5.28 g).

Step 5:

Process A: (3R,4S)-N-Cyclopropyl-4-hydroxymethyl-1-[(1S)-1-phenylethyl]pyrrolidine-3-carboxamide (1.49 g) was dissolved in toluene (15 mL). To this solution, a borane/dimethyl sulfide complex (0.65 mL) was added and the mixture was refluxed for 6 hours while being stirred. After the reaction mixture was allowed to cool to room temperature, a 10% aqueous solution of sodium carbonate (12.4 mL) was added and the mixture was stirred at 100° C. for 1 hour. The toluene layer was separated, washed with water (10 mL), and dried over anhydrous sodium sulfate, followed by addition of di-tert-butyldicarbonate (1.13 g) and stirring at room temperature for 30 min. The mixture was then allowed to stand overnight. Subsequently, the reaction mixture was concentrated under reduced pressure and the resulting residue was purified by silica gel column chromatography (eluant: hexane: ethyl acetate=1:1) to give (3R,4S)-3-[(N-tert-butoxycarbonyl-N-cyclopropyl)amino]methyl-4-hydroxymethyl-1-[(1S)-1-phenylethyl]pyrrolidine as pale brown crystals (1.50 g).

Process B: (3R,4S)-3-[(N-tert-Butoxycarbonyl-N-cyclopropyl)amino]methyl-4-(tert-butyldimethylsilyl)oxymethyl-1-[(1S)-1-phenylethyl]pyrrolidine (3.02 g) was dissolved in tetrahydrofuran (45 mL). While the solution was chilled in an ice water bath, tetrabutylammonium fluoride (1 mol/L tetrahydrofuran solution, 7.42 ml) was added dropwise and the mixture was stirred at room temperature for 2 hours, followed by addition of saturated brine (60 mL) and extraction with ethyl acetate (2×150 mL). The ethyl acetate layers were combined, washed with saturated brine (2×100 mL), dried over anhydrous sodium sulfate, and concentrated under reduced pressure. The residue was dissolved in ethyl acetate (10 mL) and the resulting crystals were filtered, washed with small amounts of ethyl acetate, and dried under reduced pressure to give (3R,4S)-3-[(N-tert-butoxycarbonyl-N-cyclopropyl)amino]methyl-4-hydroxymethyl-1-[(1S)-1-phenylethyl]pyrrolidine as white crystals (781 mg). The filtrate and the washings were then combined and were concentrated under reduced pressure. The resulting residue was purified by silica gel column chromatography (eluant: hexane: ethyl acetate=1:1) to give additional (3R,4S)-3-[(N-tert-butoxycarbonyl-N-cyclopropyl)amino]methyl-4-hydroxymethyl-1-[(1S)-1-phenylethyl]pyrrolidine (1.43 g).

MS (EI) m/z: 374 (M+).

elemental analysis (%)

Calcd for $C_{22}H_{34}N_2O_3$: C, 70.55; H, 9.15; N, 7.48. Found: C, 70.56; H, 9.29; N, 7.52.

Step 6:

(3R,4S)-3-[(N-tert-Butoxycarbonyl-N-cyclopropyl)amino]methyl-4-hydroxymethyl-1-[(1S)-1-phenylethyl]pyrrolidine (2.66 g) was dissolved in dichloromethane (40 mL). While this solution was chilled in a salt/ice bath, triethylamine (1.05 mL) was added, followed by dropwise addition of methanesulfonyl chloride (0.58 mL). The reaction mixture was stirred at −5° C. or below for 30 min, then washed with water, dried over anhydrous sodium sulfate, and concentrated under reduced pressure. The resulting residue was dissolved in tetrahydrofuran (21 mL) and tetrabutylammonium fluoride (1 mol/L tetrahydrofuran solution, 21.3 mL) was added. The mixture was then refluxed for 2 hours while being stirred. Subsequently, the reaction mixture was concentrated under reduced pressure and the residue was dissolved in ethyl acetate (200 mL). The solution was washed with water (2×50 mL), dried over anhydrous sodium sulfate, and concentrated under reduced pressure. The resulting residue was purified by silica gel column chromatography (eluant: hexane: ethyl acetate=4:1->1:1) to give (3R,4S)-3-[(N-tert-butoxycarbonyl-N-cyclopropyl)amino]methyl-4-fluoromethyl-1-[(1S)-1-phenylethyl]pyrrolidine as a pale brown tar (1.13 g).

MS (EI) m/z: 376 (M$^+$)

Step 7:

(3R,4S)-3-[(N-tert-Butoxycarbonyl-N-cyclopropyl)amino]methyl-4-fluoromethyl-1-[(1S)-1-phenylethyl]pyrrolidine (1.10 g) was dissolved in methanol (20 mL). To this solution, 10% palladium carbon (230 mg) suspended in water (4 mL) and then ammonium formate (921 mg) were added and the mixture was refluxed for 90 min while being stirred. The catalyst in the reaction mixture was filtered through a Celite pad and the catalyst and the Celite pad were washed with 20% aqueous methanol. The filtrate and the washings were combined and concentrated under reduced pressure. Water (20 mL) was then added to the residue and while the solution was chilled in an ice water bath, a 30% aqueous solution of sodium hydroxide was added to make the solution basic (pH 14) and the basic solution was extracted with dichloromethane (50 mL×2). The dichloromethane layers were combined, washed with water (2×20 mL), dried over anhydrous sodium sulfate, and concentrated under reduced pressure. The resulting residue was purified by silica gel column chromatography (eluant: dichloromethane: methanol=20:1) to give (3R,4S)-3-[(N-tert-butoxycarbonyl-N-cyclopropyl)amino]methyl-4-fluoromethylpyrrolidine as a pale brown tar (684 mg).

MS (EI) m/z: 272 (M$^+$).

Reference Example 14

Synthesis of (3R,4R)-3-cyclopropylaminomethyl-4-methylpyrrolidine-trifluoroacetate Step 1:

1-Benzyl-4-(R)-methyl-3-(R)-[(4-(S)-phenyl-2-oxazolidinon-3-yl)carbonyl]pyrrolidine (150 g) was dissolved in cyclopropylamine (650 mL). The mixture was stirred at room temperature for 23 hours and was concentrated under reduced pressure. Diisopropyl ether (800 mL) was added to the residue and the solution was stirred at room temperature for 70 min. The resulting crystals were filtered. The collected crystals were then dissolved in dichloromethane (800 mL) and the solution was extracted with 1 mol/L hydrochloric acid (2×400 mL). The layers of 1 mol/L hydrochloric acid were combined. While the combined layer was chilled in an ice water bath, a 30% aqueous NaOH solution was added to make the solution basic (pH 13). The resulting crystals were filtered, washed sequentially with water and diisopropyl ether, and dried under reduced pressure to give (3R,4R)-1-benzyl-N-cyclopropyl-4-methyl-3-pyrrolidinecarboxamide as white crystals (52.2 g).

Step 2:

(3R,4R)-1-Benzyl-N-cyclopropyl-4-methyl-3-pyrrolidinecarboxamide (70.0 g) was dissolved in toluene (700 mL). While this solution was chilled in an ice water bath, a borane/dimethyl sulfate complex (90%, 34.3 mL) was added dropwise. The mixture was then stirred for 15 min, was refluxed and was allowed to cool to room temperature. A 10% aqueous Na$_2$CO$_3$ solution (400 mL) was added, and the mixture was stirred at 100° C. for 2 hours and was then allowed to cool to room temperature. The toluene layer was separated, washed with water (2×250 mL), dried over anhydrous sodium sulfate, and concentrated under reduced pressure. The resulting residue was purified by distillation under reduced pressure to give (3S,4R)-1-benzyl-3-cyclopropylaminomethyl-4-methylpyrrolidine as a colorless oil (62.1 g).

Step 3:

(3S,4R)-1-Benzyl-3-cyclopropylaminomethyl-4-methylpyrrolidine (25.0 g) was dissolved in ethanol (200 mL). To this solution, trifluoroacetic acid (15.7 mL) and 10% palladium carbon (12.5 g) were added and the mixture was stirred at room temperature under hydrogen pressure of 3.9×10$^5$ Pa for 9 hours. The catalyst in the reaction mixture was filtered and the collected catalyst was washed with a 25% aqueous ethanol (300 mL). The filtrate and the washings were combined and concentrated under reduced pressure. The remaining pale brown crystals were suspended in tetrahydrofuran (100 mL) and were filtered. The collected crystals were washed with tetrahydrofuran and dried under reduced pressure to give (3R,4R)-3-cyclopropylaminomethyl-4-methylpyrrolidine-trifluoroacetate as white crystals (34.1 g).

Reference Example 15

Synthesis of (3R,4S)-3-cyclopropylaminomethyl-4-fluoropyrrolidine (Process III)

Step 1:

Process A: (3R,4S)-Deoxy-3-C—(N-benzyloxycarbonyl)aminomethyl-1,2:5,6-di-O-isopropylidene-α-D-allofuranose (14.1 g) was dissolved in tetrahydrofuran (150 mL). To this solution, 1 mol/L hydrochloric acid (150 mL) was added and the mixture was stirred at 60° C. for 1.5 hours. Subsequently, the reaction mixture was concentrated under reduced pressure to give a brown foamy material (10.1 g).

The brown foamy material (9.64 g) was mixed with dichloromethane (100 mL), and triethylsilane (9.40 mL) and a trifluoroboron/diethyl ether complex (3.80 mL) were added. The reaction mixture was stirred at room temperature for 2 hours, refluxed for 1 hour, and then concentrated under reduced pressure. The residue was dissolved in a mixture of ethanol (300 mL) and water (100 mL), followed by addition of sodium periodate (13.9 g) and stirring at room temperature for 1 hour. The insoluble material in the reaction mixture was then filtered and washed with ethanol (30 mL). The filtrate and the washings were combined and sodium borohydride (1.33 g) was added to the combined solution. The mixture was stirred at room temperature for 1 hour, followed by additional sodium borohydride (0.61 g) and further stirring at room temperature for 1.5 hours. The insoluble material in the reaction mixture was filtered and washed with ethanol (30 mL). The filtrate and the washings were combined and concentrated under reduced pressure. The resulting residue was dissolved in ethyl acetate (300 mL), washed with saturated brine (2×100 mL), dried over anhydrous sodium sulfate, and concentrated under reduced pressure. The resulting residue was purified by silica gel column chromatography (eluant: ethyl acetate: methanol=20:1) to give (3R,4R)-(1-benzyloxycarbonyl-4-hydroxypyrrolidin-3-yl)methanol as a pale yellow tar (5.07 g).

Process B: (3R,4S)-4-[(1S,2R)-1,2,3-Trihydroxypropyl]pyrrolidin-3-ol (0.76 g) and triethylamine (0.60 mL) were dissolved in N,N-dimethylacetamide (12 mL). While this solution was chilled in an ice water bath, benzyl chloroformate (0.58 mL) was added dropwise and the mixture was stirred for 1 hour, followed by addition of tetrahydrofuran (12 mL) and further stirring for 30 min. The insoluble material in the reaction mixture was then filtered and washed with a 1:1 mixture of N,N-dimethylacetamide and tetrahydrofuran. The filtrate and the washings were combined and concentrated under reduced pressure. The resulting residue was dissolved in a mixture of ethanol (32 mL) and water (7 mL), followed by addition of sodium periodate (1.85 g) and stirring at room temperature for 1 hour. The insoluble material in the reaction mixture was filtered and washed with ethanol. The filtrate and the washings were combined and sodium borohydride (242 mg) was added. This was followed by stirring at room temperature for 1 hour, addition of acetone (2 mL) and concentration under reduced pressure. The resulting residue was dissolved in ethyl acetate (100 mL), washed with saturated brine (2×20 mL), dried over anhydrous sodium sulfate, and concentrated under reduced pressure. The resulting residue was purified by silica gel column chromatography (eluant: ethyl acetate: methanol=20:1) to give (3R,4R)-(1-benzyloxycarbonyl-4-hydroxypyrrolidin-3-yl)methanol as a milky white syrup (828 mg).

Step 2:

(3R,4R)-(1-Benzyloxycarbonyl-4-hydroxypyrrolidin-3-yl)methanol (503 mg) and triphenylphosphine (577 mg) were dissolved in N,N-dimethylacetamide (10 mL) While this solution was chilled in an ice water bath, carbon tetrabromide (730 mg) in dichloromethane (2 mL) was added dropwise. After the reaction mixture was stirred at room temperature for 5 hours, methanol (1 mL) was added and the mixture was concentrated under reduced pressure. The residue was dissolved in ethyl acetate (50 mL), washed with saturated brine (2×10 mL), dried over anhydrous sodium sulfate, and concentrated under reduced pressure. The resultant residue was purified by silica gel column chromatography (eluant: ethyl acetate: hexane=2:1) to give (3S,4R)-1-benzyloxycarbonyl-3-bromomethyl-4-hydroxypyrrolidine as a milky white syrup (503 mg).

MS (FAB$^+$): m/z=314 (M$^+$+H).

HRMS (FAB$^+$)

Calcd for $C_{13}H_{17}BrNO_3$(M$^+$+H): 314.0392. Found 314.0346.

Step 3

Process A: (3S,4R)-1-Benzyloxycarbonyl-3-bromomethyl-4-hydroxypyrrolidine (2.70 g) was dissolved in dichloromethane (60 mL). While the solution was chilled in an ice water bath, diethylaminosulfur trifluoride (2.30 mL) was added dropwise and the mixture was stirred at room temperature for 20 hours. Following addition of a saturated aqueous solution of sodium bicarbonate (30 mL) in an ice water bath, the dichloromethane layer was separated. The dichloromethane layer was washed sequentially with a saturated aqueous solution of sodium bicarbonate (30 mL) and saturated brine (30 mL), dried over anhydrous sodium sulfate, and concentrated under reduced pressure. The resulting residue was purified by silica gel column chromatography (eluant: hexane: ethyl acetate=2:1) to give (3S,4S)-1-benzyloxycarbonyl-3-bromomethyl-4-fluoropyrrolidine as a yellow-brown tar (2.20 g).

Process B: (3S,4R)-1-Benzyloxycarbonyl-3-bromomethyl-4-hydroxypyrrolidine (492 mg) was dissolved in toluene (1 mL). To this solution, 1,8-diazabicyclo[5.4.0]undec-7-ene (0.35 mL) was added and perfluoro-1-octanesulfonylfluoride (0.42 mL) was subsequently added dropwise while the mixture was chilled in an ice water bath. The reaction mixture was stirred at 2° C. for 30 min and then at room temperature for 5 hours. Subsequently, the mixture was poured on a silica gel pad and was eluted with ethyl acetate (80 mL). The eluate was concentrated under reduced pressure and the resulting residue was purified by silica gel column chromatography (eluant: hexane: ethyl acetate=2:1) to give (3S,4S)-1-benzyloxycarbonyl-3-bromomethyl-4-fluoropyrrolidine as a milky white syrup (421 mg).

MS (FAB$^+$): m/z=316 (M$^+$+H).

HRMS (FAB$^+$)

Calcd for $C_{13}H_{16}BrFNO_2$(M$^+$+H): 316.0348. Found: 316.0362.

Step 4:

(3S,4S)-1-Benzyloxycarbonyl-3-bromomethyl-4-fluoropyrrolidine (415 mg), cyclopropylamine (0.91 mL) and acetonitrile (3 mL) were mixed together. The mixture was stirred at 80° C. for 6 hours and was subsequently concentrated under reduced pressure. To the resulting residue, cyclopropylamine (4.55 mL) was added and the mixture was again stirred at 80° C. for 6 hours and was concentrated under reduced pressure. The residue was dissolved in ethyl acetate (15 mL), washed with saturated brine (2×5 mL), dried over anhydrous sodium sulfate, and concentrated under reduced pressure. The resulting residue was purified by silica gel column chromatography (eluant: hexane: ethyl acetate=2:1) to give (3S,4S)-1-benzyloxycarbonyl-3-cyclopropylaminomethyl-4-fluoropyrrolidine as a pale brown oil (239 mg).

MS (FAB$^+$): m/z=293 (M$^+$+H).

HRMS (FAB$^+$)

Calcd for $C_{16}H_{22}FN_2O_2$(M$^+$+H): 293.1665. Found: 293.1698.

Step 5:

(3S,4S)-1-Benzyloxycarbonyl-3-cyclopropylaminomethyl-4-fluoropyrrolidine (2.29 g) was dissolved in ethanol (25 mL). To this solution, 10% palladium carbon (229 mg) was added and the mixture was stirred at room temperature for 1.5 hours under a stream of hydrogen gas. The catalyst in the reaction mixture was filtered and was washed with ethanol. The filtrate and the washings were combined and concentrated under reduced pressure. The resulting residue was distilled under reduced pressure to give (3R,4S)-3-cyclopropylaminomethyl-4-fluoropyrrolidine as a colorless oil (1.14 g). This compound was identical to the compound obtained in Reference Example 8 (Process I).

Reference Example 16

Synthesis of (3R,4S)-3-cyclopropylaminomethyl-4-fluoropyrrolidine (Process IV)

Step 1:

(3R,4R)-(1-tert-Butoxycarbonyl-4-hydroxypyrrolidin-3-yl)methanol (3.64 g) and triphenylphosphine (4.41 g) were dissolved in N,N-dimethylacetamide (84 mL). While the solution was chilled in an ice water bath, carbon tetrabromide (5.57 g) in dichloromethane (16 mL) was added dropwise. The mixture was stirred at room temperature for 13 hours, followed by addition of methanol (8 mL) and concentration under reduced pressure. The resulting residue was dissolved in ethyl acetate (300 mL), washed sequentially with water (100 mL) and saturated brine (100 mL), dried over anhydrous sodium sulfate, and concentrated under reduced pressure. The resulting residue was purified by silica gel column chromatography (eluant: ethyl acetate: hexane=2:1) to give (3S,4R)-3-bromomethyl-1-tert-butoxycarbonyl-4-hydroxypyrrolidine as a milky white syrup (3.17 g).

MS (EI$^+$): m/z=279 (M$^+$).

HRMS (EI$^+$)

Calcd for $C_{10}H_{18}BrNO_3$(M$^+$): 279.0470.

Found: 279.0471.

Step 2:

Process A: (3S,4R)-3-Bromomethyl-1-tert-butoxycarbonyl-4-hydroxypyrrolidine (1.97 g) was dissolved in dichloromethane (50 mL). While this solution was chilled in an ice water bath, diethylaminosulfur trifluoride (1.90 mL) was added dropwise and the mixture was stirred at room temperature for 19 hours. Subsequently, while the reaction mixture was chilled in an ice water bath, a saturated aqueous solution of sodium bicarbonate (40 mL) was added and the dichloromethane layer was separated. The dichloromethane layer was then washed sequentially with a saturated aqueous solution of sodium bicarbonate (20 mL) and saturated brine (20 mL), dried over anhydrous sodium sulfate, and concentrated under reduced pressure. The resulting residue was purified by silica gel column chromatography (eluant: hexane: ethyl acetate=2:1) to give (3S,4S)-3-bromomethyl-1-tert-butoxycarbonyl-4-fluoropyrrolidine as a yellow-brown tar (1.64 g).

Process B: (3S,4R)-3-Bromomethyl-1-tert-butoxycarbonyl-4-hydroxypyrrolidine (561 mg) was dissolved in toluene (20 mL). To this solution, 1,8-diazabicyclo[5.4.0]undec-7-ene (0.50 mL) was added and perfluoro-1-octanesulfonylfluoride (0.93 mL) was then added dropwise while the mixture was chilled in an ice water bath. After stirred at 2° C. for 1 hour, the reaction mixture was poured on a silica gel pad and was eluted with ethyl acetate (100 mL). The eluate was concentrated under reduced pressure and the resulting residue was purified by silica gel column chromatography (eluant: hexane: ethyl acetate=2:1) to give (3S,4S)-3-bromomethyl-1-tert-butoxycarbonyl-4-fluoropyrrolidine as a yellow oil (447 mg).

MS (EI$^+$): m/z=281 (M$^+$).
HRMS (EI$^+$) Calcd for $C_{10}H_{17}BrFNO_2$(M$^+$): 281.0427. Found: 281.0470.

Step 3:

(3S,4S)-3-Bromomethyl-1-tert-butoxycarbonyl-4-fluoropyrrolidine (1.91 g) was mixed with cyclopropylamine (23.6 mL). The mixture was stirred at 80° C. for 23 hours and was concentrated under reduced pressure. The residue was dissolved in ethyl acetate (100 mL), washed with saturated brine (2×20 mL), dried over anhydrous sodium sulfate, and concentrated under reduced pressure. The resulting residue was purified by silica gel column chromatography (eluant: hexane: ethyl acetate=2:1) to give (3S,4S)-1-tert-butoxycarbonyl-3-cyclopropylaminomethyl-4-fluoropyrrolidine as a pale brown oil (1.67 g).

MS (EI$^+$): m/z=258 (M$^+$).
HRMS (EI$^+$)
Calcd for $C_{13}H_{23}FN_2O_2$(M$^+$): 258.1744.
Found: 258.1756.

Step 4:

(3S,4S)-1-tert-Butoxycarbonyl-3-cyclopropylaminomethyl-4-fluoropyrrolidine (1.81 g) was dissolved in tetrahydrofuran (10 mL). To this solution, trifluoroacetic acid (5.40 mL) was added. The mixture was then stirred at room temperature for 4 hours and was allowed to stand overnight. Subsequently, the reaction mixture was concentrated under reduced pressure and the resulting residue was dissolved in trifluoroacetic acid (10.8 mL). This was followed by stirring at room temperature for 1.5 hours and concentration under reduced pressure. To the resulting residue, a mixture of diisopropyl ether and tetrahydrofuran was added and the resulting crystals were filtered. Washing the collected crystals with diisopropyl ether gave (3R,4S)-3-cyclopropylaminomethyl-4-fluoropyrrolidine di-trifluoroacetate (2.19 g).

(3R,4S)-3-Cyclopropylaminomethyl-4-fluoropyrrolidine di-trifluoroacetate (2.09 g) was dissolved in water (5 mL) and a 30% aqueous solution of sodium hydroxide was added to make the solution basic. The mixture was then extracted with dichloromethane (3×15 mL). The dichloromethane extracts were combined, dried over anhydrous sodium sulfate, and concentrated under reduced pressure. The resulting residue was distilled under reduced pressure to give (3R,4S)-3-cyclopropylaminomethyl-4-fluoropyrrolidine as a colorless oil (785 mg). This compound was identical to the compound obtained in Reference Example 8.

Example 1

Synthesis of 1-cyclopropyl-7-[(3S,4S)-3-cyclopropylaminomethyl-4-fluoro-1-pyrrolidinyl]-6-fluoro-1,4-dihydro-8-methoxy-4-oxo-3-qunolinecarboxylic acid Bis(acetato-O)(1-cyclopropyl-6,7-difluoro-1,4-dihydro-8-methoxy-4-oxo-3-quinolinecarboxylato-O$^3$,O$^4$)boron (73.0 mg), (3R,4S)-3-cyclopropylaminomethyl-4-fluoropyrrolidine (30.0 mg), triethylamine (29.0 μL) and acetonitrile (2 mL) were mixed together. The reaction mixture was stirred at 60° C. for 3 hours and was concentrated under reduced pressure. The resulting residue was purified by silica gel column chromatography (ethyl acetate: methanol=5:1) and the eluate was dissolved in 5% aqueous acetic acid (2 mL), followed by stirring at 80° C. for 2 hours. Subsequently, the reaction mixture was washed with ethyl acetate (2×1 mL) and was neutralized with a 2 mol/L aqueous solution of sodium hydroxide. The crystallized solid was filtered, washed with small amounts of water, and dried under reduced pressure to give 1-cyclopropyl-7-[(3S,4S)-3-cyclopropylaminomethyl-4-fluoro-1-pyrrolidinyl]-6-fluoro-1,4-dihydro-8-methoxy-4-oxo-3-quinolinecarboxylic acid as a pale brown solid (31.6 mg).

MS(FAB$^+$) m/z: 434(MH$^+$)
HRMS(FAB$^+$)
Calcd for $C_{22}H_{26}F_2N_3O_4$: 434.1891. Found: 434.1913.

Example 2

Synthesis of 1-cyclopropyl-7-[(3S,4S)-3-cyclopropylaminomethyl-4-fluoro-1-pyrrolidinyl]-1,4-dihydro-8-methoxy-4-oxo-3-quinolinecarboxylic acid Using bis(acetato-O) (1-cyclopropyl-7-fluoro-1,4-dihydro-8-methoxy-4-oxo-3-quinolinecarboxylato-O$^3$,O$^4$)boron (70.0 mg) and (3R,4S)-3-cyclopropylaminomethyl-4-fluoropyrrolidine (30.0 mg), the same procedure was followed as in Example 1 to give 1-cyclopropyl-7-[(3S,4S)-3-cyclopropylaminomethyl-4-fluoro-1-pyrrolidinyl]-1,4-dihydro-8-methoxy-4-oxo-3-quinolinecarboxylic acid as a pale brown solid (41.0 mg).

MS(EI) m/z: 415(M$^+$)
HRMS(EI)
Calcd for $C_{22}H_{26}FN_3O_4$: 415.1907.
Found: 415.1881.

Example 3

Synthesis of 1-cyclopropyl-7-[(3S,4S)-3-cyclopropylaminomethyl-4-fluoro-1-pyrrolidinyl]-6-fluoro-8-difluoromethoxy-1,4-dihydro-4-oxo-3-quinolinecarboxylic acid Using bis(acetato-O) (1-cyclopropyl-6,7-difluoro-8-difluoromethoxy-1,4-dihydro-4-oxo-3-quinolinecarboxylato-O$^3$,O$^4$)boron (79.4 mg) and (3R,4S)-3-cyclopropylaminomethyl-4-fluoropyrrolidine (30.0 mg), the same procedure was followed as in Example 1 to give 1-cyclopropyl-7-[(3S,4S)-3-cyclopropylaminomethyl-4-fluoro-1-pyrrolidinyl]-6-fluoro-8-difluoromethoxy-1,4-dihydro-4-oxo-3-quinolinecarboxylic acid as a white solid (33.4 mg).

MS(EI) m/z: 469(M+)
HRMS(EI)
Calcd for $C_{22}H_{23}F_4N_3O_4$: 469.1625. Found: 469.1642.

Example 4

Synthesis of 1-cyclopropyl-7-[(3S,4S)-3-cyclopropylaminomethyl-4-fluoro-1-pyrrolidinyl]-8-difluoromethoxy-1,4-dihydro-4-oxo-3-quinolinecarboxylic acid Using bis(acetato-O)(1-cyclopropyl-7-fluoro-8-difluoromethoxy-1,4-dihydro-4-oxo-3-quinolinecarboxylato-$O^3$,$O^4$)boron (76.4 mg) and (3R,4S)-3-cyclopropylaminomethyl-4-fluoropyrrolidine (30.0 mg), the same procedure was followed as in Example 1 to give 1-cyclopropyl-7-[(3S,4S)-3-cyclopropylaminomethyl-4-fluoro-1-pyrrolidinyl]-8-difluoromethoxy-1,4-dihydro-4-oxo-3-quinolinecarboxylic acid as a white solid (55.4 mg).
MS(EI) m/z: 451(M+)
HRMS(EI)
Calcd for $C_{22}H_{24}F_3N_3O_4$: 451.1719.
Found: 451.1681.

Example 5

Synthesis of 1-cyclopropyl-7-(trans-3-cyclopropylaminomethyl-4-methyl-1-pyrrolidinyl)-6-fluoro-1,4-dihydro-8-methoxy-4-oxo-3-quinolinecarboxylic acid Using bis(acetato-O)(1-cyclopropyl-6,7-difluoro-1,4-dihydro-8-methoxy-4-oxo-3-quinolinecarboxylato-$O^3$, $O^4$)boron (300 mg) and trans-3-cyclopropylaminomethyl-4-methylpyrrolidine (135 mg), the same procedure was followed as in Example 1 to give 1-cyclopropyl-7-(trans-3-cyclopropylaminomethyl-4-methyl-1-pyrrolidinyl)-6-fluoro-1,4-dihydro-8-methoxy-4-oxo-3-quinolinecarboxylic acid as pale yellow crystals (208 mg).
MS(EI) m/z: 429(M+)

elemental analysis (%)
Calcd for $C_{23}H_{28}FN_3O_4$: C, 64.32; H, 6.57; N, 9.78. Found: C, 63.95; H, 6.57; N, 9.69.

Example 6

Synthesis of 1-cyclopropyl-7-(trans-3-cyclopropylaminomethyl-4-trifluoromethyl-1-pyrrolidinyl)-6-fluoro-1,4-dihydro-8-methoxy-4-oxo-3-quinolinecarboxylic acid Using bis(acetato-O)(1-cyclopropyl-6,7-difluoro-1,4-dihydro-8-methoxy-4-oxo-3-quinolinecarboxylato-$O^3$,$O^4$)boron (300 mg) and trans-3-cyclopropylaminomethyl-4-trifluoromethylpyrrolidine (177 mg), the same procedure was followed as in Example 1 to give 1-cyclopropyl-7-(trans-3-cyclopropylaminomethyl-4-trifluoromethyl-1-pyrrolidinyl)-6-fluoro-1,4-dihydro-8-methoxy-4-oxo-3-quinolinecarboxylic acid as white crystals (129 mg).
MS(EI) m/z: 483(M+)

elemental analysis (%)
Calcd for $C_{23}H_{25}F_4N_3O_4$: C, 57.14; H, 5.21; N, 8.69. Found: C, 56.95; H, 5.25; N, 8.64.

Example 7

Synthesis of 1-cyclopropyl-7-[(3S,4R)-3-cyclopropylaminomethyl-4-methyl-1-pyrrolidinyl]-1,4-dihydro-8-methoxy-4-oxo-3-quinolinecarboxylic acid Using bis(acetato-O)(1-cyclopropyl-7-fluoro-1,4-dihydro-8-methoxy-4-oxo-3-quinolinecarboxylato-$O^3$,$O^4$)boron (300 mg) and (3R,4R)-3-cyclopropylaminomethyl-4-methylpyrrolidine (137 mg), the same procedure was followed as in Example 1 to give 1-cyclopropyl-7-[(3S,4R)-3-cyclopropylaminomethyl-4-methyl-1-pyrrolidinyl]-1,4-dihydro-8-methoxy-4-oxo-3-quinolinecarboxylic acid as yellow crystals (181 mg).
MS(EI) m/z: 411(M+)

elemental analysis (%)
Calcd for $C_{23}H_{29}N_3O_4$: C, 67.13; H, 7.10; N, 10.21. Found: C, 67.11; H, 7.11; N, 10.24

Example 8

Synthesis of 1-cyclopropyl-7-[(3R,4S)-3-cyclopropylaminomethyl-4-methyl-1-pyrrolidinyl]-1,4-dihydro-8-methoxy-4-oxo-3-quinolinecarboxylic acid Using bis(acetato-O)(1-cyclopropyl-7-fluoro-1,4-dihydro-8-methoxy-4-oxo-3-quinolinecarboxylato-$O^3$,$O^4$)boron (300 mg) and (3S,4S)-3-cyclopropylaminomethyl-4-methylpyrrolidine (137 mg), the same procedure was followed as in Example 1 to give 1-cyclopropyl-7-[(3R,4S)-3-cyclopropylaminomethyl-4-methyl-1-pyrrolidinyl]-1,4-dihydro-8-methoxy-4-oxo-3-quinolinecarboxylic acid as yellow prism crystals (162 mg).
MS(EI) m/z: 411(M+)

elemental analysis (%)
Calcd for $C_{23}H_{29}N_3O_4$: C, 67.13; H, 7.10; N, 10.21. Found: C, 67.04; H, 7.15; N, 10.28.

Example 9

Synthesis of 1-cyclopropyl-7-[(3S,4R)-3-cyclopropylaminomethyl-4-fluoro-1-pyrrolidinyl]-6-fluoro-1,4-dihydro-8-methoxy-4-oxo-3-quinolinecarboxylic acid Using bis(acetato-O) (1-cyclopropyl-6,7-difluoro-1,4-dihydro-8-methoxy-4-oxo-3-quinolinecarboxylato-$O^3$, $O^4$)boron (73.0 mg) and (3R,4R)-3-cyclopropylaminomethyl-4-fluoropyrrolidine (30.0 mg), the same procedure was followed as in Example 1 to give 1-cyclopropyl-7-[(3S,4R)-3-cyclopropylaminomethyl-4-fluoro-1-pyrrolidinyl]-6-fluoro-1,4-dihydro-8-methoxy-4-oxo-3-quinolinecarboxylic acid as white crystals (45.9 mg).
MS(FAB+) m/z: 434(MH+)

elemental analysis (%)
Calcd for $C_{22}H_{25}F_2N_3O_4$: C, 60.96; H, 5.81; N, 9.69. Found: C, 60.76; H, 5.72; N, 9.32.

Example 10

Synthesis of 1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid Using bis(acetato-O)(1-cyclopropyl-6,7-difluoro-1,4-dihydro-8-methyl-4-oxo-3-quinolinecarboxylato-$O^3,O^4$)boron (200 mg) and (3R,4S)-3-cyclopropylaminomethyl-4-fluoropyrrolidine (85.4 mg), the same procedure was followed as in Example 1 to give 1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid as yellow crystals (57.1 mg).

MS(FAB$^+$) m/z: 418(MH$^+$)

HRMS(EI)

Calcd for $C_{22}H_{26}F_2N_3O_3$: 418.1942. Found: 418.1974.

Example 11

Synthesis of 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-8-methoxy-3-quinolinecarboxylic acid Using bis(acetato-O)[6,7-difluoro-1-[(1R,2S)-2-fluorocyclopropyl]-1,4-dihydro-8-methoxy-4-oxo-3-quinolinecarboxylato-$O^3,O^4$]boron (300 mg) and (3R,4S)-3-cyclopropylaminomethyl-4-fluoropyrrolidine (118 mg), the same procedure was followed as in Example 1 to give 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-8-methoxy-3-quinolinecarboxylic acid as a pale yellow solid (145 mg).

MS(FAB$^+$) m/z: 452(MH$^+$)

elemental analysis (%)

Calcd for $C_{22}H_{24}F_3N_3O_4 \cdot 0.5H_2O$: C, 57.39; H, 5.47; N, 9.31. Found: C, 57.45; H, 5.28; N, 9.06

Example 12

Synthesis of 7-[(3S,4S)-3-cyclopropylaminomethyl-4-fluoro-1-pyrrolidinyl]-6-fluoro-1-[(1R,2S)-2-fluorocyclopropyl]-8-difluoromethoxy-1,4-dihydro-4-oxo-3-quinolinecarboxylic acid Using bis(acetato-O)[6,7-difluoro-1-[(1R,2S)-2-fluorocyclopropyl]-8-difluoromethoxy-1,4-dihydro-4-oxo-3-quinolinecarboxylato-$O^3,O^4$]boron (334 mg) and (3R,4S)-3-cyclopropylaminomethyl-4-fluoropyrrolidine (122 mg), the same procedure was followed as in Example 1 to give 7-[(3S,4S)-3-cyclopropylaminomethyl-4-fluoro-1-pyrrolidinyl]-6-fluoro-1-[(1R,2S)-2-fluorocyclopropyl]-8-difluoromethoxy-1,4-dihydro-4-oxo-3-quinolinecarboxylic acid as a pale yellow solid (84.0 mg).

MS(FAB$^+$) m/z: 488(MH$^+$)

elemental analysis (%)

Calcd for $C_{22}H_{22}F_5N_3O_4$: C, 54.21; H, 4.55; N, 8.62. Found: C, 53.90; H, 4.51; N, 8.55.

Example 13

Synthesis of 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-8-methyl-3-quinolinecarboxylic acid Using bis(acetato-O) [6,7-difluoro-1-[(1R,2S)-2-fluorocyclopropyl]-1,4-dihydro-8-methyl-4-oxo-3-quinolinecarboxylato-$O^3,O^4$]boron (213 mg) and (3R,4S)-3-cyclopropylaminomethyl-4-fluoropyrrolidine (94.9 mg), the same procedure was followed as in Example 1 to give 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-8-methyl-3-quinolinecarboxylic acid as a pale yellow amorphous product (15.8 mg).

MS(FAB$^+$) m/z: 436(MH$^+$)

HRMS(EI)

Calcd for $C_{22}H_{25}F_3N_3O_3$: 436.1848. Found: 436.1878.

Example 14

Synthesis of 7-[(3S,4S)-3-cyclopropylaminomethyl-4-fluoro-1-pyrrolidinyl]-1-[(1R,2S)-2-fluorocyclopropyl]-1,4-dihydro-4-oxo-8-methoxy-3-quinolinecarboxylic acid Using bis(acetato-O) [7-fluoro-1-[(1R,2S)-2-fluorocyclopropyl]-1,4-dihydro-8-methoxy-4-oxo-3-quinolinecarboxylato-$O^3,O^4$]boron (199 mg) and (3R,4S)-3-cyclopropylaminomethyl-4-fluoropyrrolidine (81.7 mg), the same procedure was followed as in Example 1 to give 7-[(3S,4S)-3-cyclopropylaminomethyl-4-fluoro-1-pyrrolidinyl]-1-[(1R,2S)-2-fluorocyclopropyl]-1,4-dihydro-4-oxo-8-methoxy-3-quinolinecarboxylic acid as a pale yellow solid (111 mg).

MS(FAB$^+$) m/z: 434(MH$^+$)

elemental analysis (%)

Calcd for $C_{22}H_{25}F_2N_3O_4 \cdot 0.5H_2O$: C, 59.72; H, 5.92; N, 9.50. Found: C, 59.87; H, 5.71; N, 9.40.

Example 15

Synthesis of 7-[(3S,4S)-3-cyclopropylaminomethyl-4-fluoro-1-pyrrolidinyl]-1-ethyl-6-fluoro-1,4-dihydro-8-methoxy-4-oxo-3-quinolinecarboxylic acid Using bis(acetato-O)[1-ethyl-6,7-difluoro-1,4-dihydro-8-methoxy-4-oxo-3-quinolinecarboxylato-$O^3,O^4$]boron (288 mg) and (3R,4S)-3-cyclopropylaminomethyl-4-fluoropyrrolidine (122 mg), the same procedure was followed as in Example 1 to give 7-[(3S,4S)-3-cyclopropylaminomethyl-4-fluoro-1-pyrrolidinyl]-1-ethyl-6-fluoro-1,4-dihydro-8-methoxy-4-oxo-3-quinolinecarboxylic acid as pale brown crystals (135 mg).

MS(FAB$^+$) m/z: 422(MH$^+$)

elemental analysis (%)

Calcd for $C_{21}H_{25}F_2N_3O_4$: C, 59.85; H, 5.98; N, 9.97. Found: C, 59.89; H, 5.90; N, 9.97.

Example 16

Synthesis of 7-[(3S,4S)-3-cyclopropylaminomethyl-4-fluoro-1-pyrrolidinyl]-6-fluoro-1-(2-fluoroethyl)-1,4-dihydro-8-methoxy-4-oxo-3-quinolinecarboxylic acid Using bis(acetato-O)[6,7-difluoro-1-(2-fluoroethyl)-1,4-dihydro-8-methoxy-4-oxo-3-quinolinecarboxylato-$O^3$, $O^4$]boron (300 mg) and (3R,4S)-3-cyclopropylaminomethyl-4-fluoropyrrolidine (122 mg), the same procedure was followed as in Example 1 to give 7-[(3S,4S)-3-cyclopropylaminomethyl-4-fluoro-1-pyrrolidinyl]-6-fluoro-1-(2-fluoroethyl)-1,4-dihydro-8-methoxy-4-oxo-3-quinolinecarboxylic acid as pale brown crystals (112 mg).

MS(FAB$^+$) m/z: 440(MH$^+$)

elemental analysis (%)

Calcd for $C_{21}H_{24}F_3N_3O_4 \cdot 0.25H_2O$: C, 56.82; H, 5.56; N, 9.47. Found: C, 56.90; H, 5.40; N, 9.37.

Example 17

Synthesis of 1-cyclopropyl-7-[(3S,4R)-3-cyclopropylaminomethyl-4-methyl-1-pyrrolidinyl]-6-fluoro-1,4-dihydro-8-methoxy-4-oxo-3-quinolinecarboxylic acid Using bis(acetato-O)(1-cyclopropyl-6,7-difluoro-1,4-dihydro-8-methoxy-4-oxo-3-quinolinecarboxylato-$O^3$,$O^4$)boron (212 mg) and (3R,4R)-3-cyclopropylaminomethyl-4-methylpyrrolidine (84.8 mg), the same procedure was followed as in Example 1 to give 1-cyclopropyl-7-[(3S,4R)-3-cyclopropylaminomethyl-4-methyl-1-pyrrolidinyl]-6-fluoro-1,4-dihydro-8-methoxy-4-oxo-3-quinolinecarboxylic acid as a pale yellow solid (123 mg).

MS(FAB$^+$) m/z: 430(MH$^+$)

elemental analysis (%)

Calcd for $C_{23}H_{28}FN_3O_4$: C, 64.32; H, 6.57; N, 9.78. Found: C, 64.04; H, 6.53; N, 9.72.

Example 18

Synthesis of 1-cyclopropyl-7-[(3S,4S)-3-cyclopropylaminomethyl-4-methyl-1-pyrrolidinyl]-6-fluoro-1,4-dihydro-8-methoxy-4-oxo-3-quinolinecarboxylic acid Using bis(acetato-O)(1-cyclopropyl-6,7-difluoro-1,4-dihydro-8-methoxy-4-oxo-3-quinolinecarboxylato-$O^3$, $O^4$)boron (212 mg) and (3S,4S)-3-cyclopropylaminomethyl-4-methylpyrrolidine (84.8 mg), the same procedure was followed as in Example 1 to give 1-cyclopropyl-7-[(3S,4S)-3-cyclopropylaminomethyl-4-methyl-1-pyrrolidinyl]-6-fluoro-1,4-dihydro-8-methoxy-4-oxo-3-quinolinecarboxylic acid as a pale yellow solid (106 mg).

MS(FAB$^+$) m/z: 430(MH$^+$)

elemental analysis (%)

Calcd for $C_{23}H_{28}FN_3O_4 \cdot 0.75H_2O$: C, 62.36; H, 6.71; N, 9.48. Found: C, 62.65; H, 6.53; N, 9.44.

Example 19

Synthesis of 1-cyclopropyl-7-[(3R,4S)-3-cyclopropylaminomethyl-4-methyl-1-pyrrolidinyl]-6-fluoro-1,4-dihydro-8-methoxy-4-oxo-3-quinolinecarboxylic acid Using bis(acetato-O)(1-cyclopropyl-6,7-difluoro-1,4-dihydro-8-methoxy-4-oxo-3-quinolinecarboxylato-$O^3$, $O^4$)boron (212 mg) and (3S,4S)-3-cyclopropylaminomethyl-4-methylpyrrolidine (84.8 mg), the same procedure was followed as in Example 1 to give 1-cyclopropyl-7-[(3R,4S)-3-cyclopropylaminomethyl-4-methyl-1-pyrrolidinyl]-6-fluoro-1,4-dihydro-8-methoxy-4-oxo-3-quinolinecarboxylic acid as a pale yellow powder (131 mg).

MS(FAB$^+$) m/z: 430(MH$^+$)

elemental analysis (%)

Calcd for $C_{23}H_{28}FN_3O_4 \cdot 0.25H_2O$: C, 63.65; H, 6.62; N, 9.68. Found: C, 63.77; H, 6.54; N, 9.64.

Example 20

Synthesis of 1-cyclopropyl-7-[(3R,4R)-3-cyclopropylaminomethyl-4-methyl-1-pyrrolidinyl]-6-fluoro-1,4-dihydro-8-methoxy-4-oxo-3-quinolinecarboxylic acid Using bis(acetato-O)(1-cyclopropyl-6,7-difluoro-1,4-dihydro-8-methoxy-4-oxo-3-quinolinecarboxylato-$O^3$, $O^4$)boron (212 mg) and (3S,4R)-3-cyclopropylaminomethyl-4-methylpyrrolidine (84.8 mg), the same procedure was followed as in Example 1 to give 1-cyclopropyl-7-[(3R,4R)-3-cyclopropylaminomethyl-4-methyl-1-pyrrolidinyl]-6-fluoro-1,4-dihydro-8-methoxy-4-oxo-3-quinolinecarboxylic acid as a pale yellow powder (85.3 mg).

MS(FAB$^+$) m/z: 430(MH$^+$)

elemental analysis (%)

Calcd for $C_{23}H_{28}FN_3O_4 \cdot 0.5H_2O$: C, 63.00; H, 6.67; N, 9.58. Found: C, 62.89; H, 6.43; N, 9.58.

Example 21

Synthesis of 7-[(3S,4R)-3-cyclopropylaminomethyl-4-methyl-1-pyrrolidinyl]-6-fluoro-1-[(1R,2S)-2-fluorocyclopropyl]-1,4-dihydro-8-methoxy-4-oxo-3-quinolinecarboxylic acid Using bis(acetato-O)[6,7-difluoro-1-[(1R,2S)-2-fluorocyclopropyl]-1,4-dihydro-8-methoxy-4-oxo-3-quinolinecarboxylato-$O^3$,$O^4$]boron (130 mg) and (3R,4R)-3-cyclopropylaminomethyl-4-methylpyrrolidine (50.0 mg), the same procedure was followed as in Example 1 to give 7-[(3S,4R)-3-cyclopropylaminomethyl-4-methyl-1-pyrrolidinyl]-6-fluoro-1-[(1R,2S)-2-fluorocyclopropyl]-1,4-dihydro-8-methoxy-4-oxo-3-quinolinecarboxylic acid as a pale yellow solid (45.7 mg).

MS(FAB$^+$) m/z: 448(MH$^+$)

elemental analysis (%)

Calcd for $C_{23}H_{27}F_2N_3O_4 \cdot 0.5H_2O$: C, 60.52; H, 6.18; N, 9.21. Found: C, 60.57; H, 6.01; N, 9.17.

Example 22

Synthesis of 7-[(3S,4S)-3-cyclopropylaminomethyl-4-methyl-1-pyrrolidinyl]-6-fluoro-1-[(1R,2S)-2-fluorocyclopropyl]-1,4-dihydro-8-methoxy-4-oxo-3-quinolinecarboxylic acid Using bis(acetato-O)[6,7-difluoro-1-[(1R,2S)-2-fluorocyclopropyl]-1,4-dihydro-8-methoxy-4-oxo-3-quinolinecarboxylato-$O^3,O^4$]boron (130 mg) and (3R,4S)-3-cyclopropylaminomethyl-4-methylpyrrolidine (50.0 mg), the same procedure was followed as in Example 1 to give 7-[(3S,4S)-3-cyclopropylaminomethyl-4-methyl-1-pyrrolidinyl]-6-fluoro-1-[(1R,2S)-2-fluorocyclopropyl]-1,4-dihydro-8-methoxy-4-oxo-3-quinolinecarboxylic acid as a pale yellow solid (61.4 mg).

MS(FAB$^+$) m/z: 448(MH$^+$)

elemental analysis (%)
Calcd for $C_{23}H_{27}F_2N_3O_4 \cdot 0.25H_2O$: C, 61.12; H, 6.13; N, 9.30. Found: C, 61.08; H, 6.04; N, 9.18.

Example 23

Synthesis of 7-[(3S,4S)-3-cyclopropylaminomethyl-4-fluoro-1-pyrrolidinyl]-1-ethyl-6-fluoro-1,4-dihydro-4-oxo-3-quinolinecarboxylic) acid 1-ethyl-6,7-difluoro-1,4-dihydro-4-oxo-3-quinolinecarboxylic) acid (253 mg), (3R,4S)-3-cyclopropylaminomethyl-4-fluoropyrrolidine (174 mg), 1,8-diazabicyclo[5.4.0.]undec-7-ene (164 μL) and acetonitrile (5 mL) were mixed together. The mixture was refluxed for 3 hours while being stirred. Subsequently, the reaction mixture was concentrated under reduced pressure and water (3 mL) was added to the resulting residue. The crystallized product was filtered, washed with water, and recrystallized from ethanol to give 7-[(3S,4S)-3-cyclopropylaminomethyl-4-fluoro-1-pyrrolidinyl]-1-ethyl-6-fluoro-1,4-dihydro-4-oxo-3-quinolinecarboxylic acid as a white crystal (248 mg).

MS(FAB$^+$) m/z: 392(MH$^+$)

elemental analysis (%)
Calcd for $C_{20}H_{23}F_2N_3O_3$: C, 61.37; H, 5.92; N, 10.74. Found: C, 61.13; H, 6.10; N, 10.63.

Example 24

Synthesis of 7-[(3S,4S)-3-cyclopropylaminomethyl-4-fluoro-1-pyrrolidinyl]-1-ethyl-6,8-difluoro-1,4-dihydro-4-oxo-3-quinolinecarboxylic acid Using 1-ethyl-6,7,8-trifluoro-1,4-dihydro-4-oxo-3-quinolinecarboxylic acid (200 mg) and (3R,4S)-3-cyclopropylaminomethyl-4-fluoropyrrolidine (128 mg), the same procedure was followed as in Example 23 to give 7-[(3S,4S)-3-cyclopropylaminomethyl-4-fluoro-1-pyrrolidinyl]-1-ethyl-6,8-difluoro-1,4-dihydro-4-oxo-3-quinolinecarboxylic acid as a pale yellow crystal (140 mg).

MS(FAB$^+$) m/z: 410(MH$^+$)

elemental analysis (%)
Calcd for $C_{20}H_{22}F_3N_3O_3$: C, 58.68; H, 5.42; N, 10.26. Found: C, 58.59; H, 5.33; N, 10.22.

Example 25

Synthesis of 7-[(3S,4S)-3-cyclopropylaminomethyl-4-fluoro-1-pyrrolidinyl]-6-fluoro-1-(2-fluoroethyl)-1,4-dihydro-4-oxo-3-quinolinecarboxylic acid Using 6,7-difluoro-1-(2-fluoroethyl)-1,4-dihydro-4-oxo-3-quinolinecarboxylic acid (271 mg) and (3R,4S)-3-cyclopropylaminomethyl-4-fluoropyrrolidine (174 mg), the same procedure was followed as in Example 23 to give 7-[(3S,4S)-3-cyclopropylaminomethyl-4-fluoro-1-pyrrolidinyl]-6-fluoro-1-(2-fluoroethyl)-1,4-dihydro-4-oxo-3-quinolinecarboxylic acid as a pale yellow powder (186 mg).

MS(FAB$^+$) m/z: 410(MH$^+$)

elemental analysis (%)
Calcd for $C_{20}H_{22}F_3N_3O_3 \cdot 0.4H_2O$: C; 57.66, H; 5.52, N; 10.09 Found: C, 57.82; H, 5.31; N, 10.04.

Example 26

Synthesis of 7-[(3S,4S)-3-cyclopropylaminomethyl-4-fluoro-1-pyrrolidinyl]-6,8-difluoro-1-(2-fluoroethyl)-1,4-dihydro-4-oxo-3-quinolinecarboxylic acid Using 6,7,8-trifluoro-1-(2-fluoroethyl)-1,4-dihydro-4-oxo-3-quinolinecarboxylic acid (200 mg) and (3R,4S)-3-cyclopropylaminomethyl-4-fluoropyrrolidine (120 mg), the same procedure was followed as in Example 23 to give 7-[(3S,4S)-3-cyclopropylaminomethyl-4-fluoro-1-pyrrolidinyl]-6,8-difluoro-1-(2-fluoroethyl)-1,4-dihydro-4-oxo-3-quinolinecarboxylic acid as pale yellow crystals (98.0 mg).

MS(FAB$^+$) m/z: 428(MH$^+$)

elemental analysis (%)
Calcd for $C_{20}H_{21}F_4N_3O_3$: C, 56.21; H, 4.95; N 9.83. Found: C, 55.81; H, 4.77; N, 9.80.

Example 27

Synthesis of 7-[(3S,4S)-3-cyclopropylaminomethyl-4-fluoro-1-pyrrolidinyl]-6-fluoro-1-(2,4-difluorophenyl)-1,4-dihydro-4-oxo-1,8-naphthyridine-3-carboxylic acid Using 7-chloro-6-fluoro-1-(2,4-difluorophenyl)-1,4-dihydro-4-oxo-1,8-naphthyridine-3-carboxylic acid (355 mg) and (3R,4S)-3-cyclopropylaminomethyl-4-fluoropyrrolidine (190 mg), the same procedure was followed as in Example 23 to give 7-[(3S,4S)-3-cyclopropylaminomethyl-4-fluoro-1-pyrrolidinyl]-6-fluoro-1-(2,4-difluorophenyl)-1,4-dihydro-4-oxo-1,8-naphthyridine-3-carboxylic acid as a pale yellow powder (229 mg).

MS(FAB$^+$) m/z: 477(MH$^+$)

elemental analysis (%)
Calcd for $C_{23}H_{20}F_4N_4O_3$: C, 57.98; H, 4.23; N, 11.76. Found: C, 57.80; H, 4.10; N, 11.67.

Example 28

Synthesis of 7-[(3S,4S)-3-cyclopropylaminomethyl-4-fluoro-1-pyrrolidinyl]-6-fluoro-1-(2,4-difluorophenyl)-1,4-dihydro-4-oxo-3-quinolinecarboxylic acid Using 6,7-difluoro-1-(2,4-difluorophenyl)-1,4-dihydro-4-oxo-3-quinolinecarboxylic acid (337 mg) and (3R,4S)-3-cyclopropylaminomethyl-4-fluoropyrrolidine (174 mg), the same procedure was followed as in Example 23 to give 7-[(3S,4S)-3-cyclopropylaminomethyl-4-fluoro-1-pyrrolidinyl]-6-fluoro-1-(2,4-difluorophenyl)-1,4-dihydro-4-oxo-3-quinolinecarboxylic acid as a pale yellow powder (309 mg).
MS(FAB$^+$) m/z: 476(MH$^+$)

elemental analysis (%)
Calcd for $C_{24}H_{21}F_4N_3O_3 \cdot 0.25H_2O$: C, 60.06; H, 4.52; N, 8.76. Found: C; 60.18; H, 4.35; N, 8.84.

Example 29

Synthesis of 1-cyclopropyl-7-[(3S,4S)-3-cyclopropylaminomethyl-4-fluoro-1-pyrrolidinyl]-6-fluoro-1,4-dihydro-4-oxo-1,8-naphthyridine-3-carboxylic acid Using 7-chloro-1-cyclopropyl-6-fluoro-1,4-dihydro-4-oxo-1,8-naphthyridine-3-carboxylic acid (283 mg) and (3R,4S)-3-cyclopropylaminomethyl-4-fluoropyrrolidine (190 mg), the same procedure was followed as in Example 23 to give 1-cyclopropyl-7-[(3S,4S)-3-cyclopropylaminomethyl-4-fluoro-1-pyrrolidinyl]-6-fluoro-1,4-dihydro-4-oxo-1,8-naphthyridine-3-carboxylic acid as a white powder (79.4 mg).
MS(FAB$^+$) m/z: 405(MH$^+$)

elemental analysis (%)
Calcd for $C_{20}H_{22}F_2N_4O_3 \cdot 0.25H_2O$: C, 58.74; H, 5.55; N, 13.70. Found: C; 58.98; H, 5.34; N, 13.70.

Example 30

Synthesis of 1-cyclopropyl-7-[(3S,4S)-3-cyclopropylaminomethyl-4-fluoro-1-pyrrolidinyl]-6-fluoro-1,4-dihydro-4-oxo-3-quinolinecarboxylic acid Using 1-cyclopropyl-6,7-difluoro-1,4-dihydro-4-oxo-3-quinolinecarboxylic acid (199 mg) and (3R,4S)-3-cyclopropylaminomethyl-4-fluoropyrrolidine (131 mg), the same procedure was followed as in Example 23 to give 1-cyclopropyl-7-[(3S,4S)-3-cyclopropylaminomethyl-4-fluoro-1-pyrrolidinyl]-6-fluoro-1,4-dihydro-4-oxo-3-quinolinecarboxylic acid as pale yellow crystals (148 mg).
MS(FAB$^+$) m/z: 404(MH$^+$)

elemental analysis (%)
Calcd for $C_{21}H_{23}F_2N_3O_3$: C; 62.52, H; 5.75, N; 10.42 Found: C, 62.14; H, 5.65; N, 10.29.

Example 31

Synthesis of 1-cyclopropyl-7-[(3S,4S)-3-cyclopropylaminomethyl-4-fluoro-1-pyrrolidinyl]-6,8-difluoro-1,4-dihydro-4-oxo-3-quinolinecarboxylic acid Using 1-cyclopropyl-6,7,8-trifluoro-1,4-dihydro-4-oxo-3-quinolinecarboxylic acid (212 mg) and (3R,4S)-3-cyclopropylaminomethyl-4-fluoropyrrolidine (142 mg), the same procedure was followed as in Example 23 to give 1-cyclopropyl-7-[(3S,4S)-3-cyclopropylaminomethyl-4-fluoro-1-pyrrolidinyl]-6,8-difluoro-1,4-dihydro-4-oxo-3-quinolinecarboxylic acid as a pale yellow crystals (157 mg).
MS(FAB$^+$) m/z: 422(MH$^+$)

elemental analysis (%)
Calcd for $C_{21}H_{22}F_3N_3O_3$: C, 59.85; H, 5.26; N, 9.97. Found: C, 59.53; H, 5.25; N, 9.76.

Example 32

Synthesis of 8-chloro-1-cyclopropyl-7-[(3S,4S)-3-cyclopropylaminomethyl-4-fluoro-1-pyrrolidinyl]-6-fluoro-1,4-dihydro-4-oxo-3-quinolinecarboxylic acid Using 8-chloro-1-cyclopropyl-6,7-difluoro-1,4-dihydro-4-oxo-3-quinolinecarboxylic acid (300 mg) and (3R,4S)-3-cyclopropylaminomethyl-4-fluoropyrrolidine (174 mg), the same procedure was followed as in Example 23 to give 8-chloro-1-cyclopropyl-7-[(3S,4S)-3-cyclopropylaminomethyl-4-fluoro-1-pyrrolidinyl]-6-fluoro-1,4-dihydro-4-oxo-3-quinolinecarboxylic acid as a pale yellow solid (218 mg).
MS(FAB$^+$) m/z: 438(MH$^+$)

elemental analysis (%)
Calcd for $C_{21}H_{22}ClF_2N_3O_3 \cdot 0.2H_2O$: C, 57.13; H, 5.11; N, 9.52. Found: C, 57.19; H, 4.97; N, 9.49.

Example 33

Synthesis of 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-1,8-naphthyridine-3-carboxylic acid Using 7-chloro-6-fluoro-1-[(1R,2S)-2-fluorocyclopropyl]-1,4-dihydro-4-oxo-1,8-naphthyridine-3-carboxylic acid (200 mg) and (3R,4S)-3-cyclopropylaminomethyl-4-fluoropyrrolidine (116 mg), the same procedure was followed as in Example 23 to give 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-1,8-naphthyridine-3-carboxylic acid as pale yellow crystals (101 mg).
MS(FAB$^+$) m/z: 423(MH$^+$)

elemental analysis (%)
Calcd for $C_{22}H_{21}F_3N_4O_3 \cdot 0.25H_2O$: C, 56.27; H, 5.08; N, 13.35. Found: C, 56.40; H, 4.88; N, 13.05.

Example 34

Synthesis of 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-3-quinolinecarboxylic acid Using 6,7-difluoro-1-[(1R,2S)-2-fluorocyclopropyl]-1,4-dihydro-4-oxo-3-quinolinecarboxylic acid (283 mg) and (3R,4S)-3-cyclopropylaminomethyl-4-fluoropyrrolidine (190 mg), the same procedure was followed as in Example 23 to give 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-3-quinolinecarboxylic acid as pale yellow crystals (203 mg).
MS(FAB$^+$) m/z: 422(MH$^+$)

elemental analysis (%)
Calcd for $C_{21}H_{22}F_3N_3O_3 \cdot 0.25H_2O$: C, 59.22; H, 5.32; N, 9.87. Found: C, 59.17; H, 5.09; N, 9.78.

Example 35

Synthesis of 7-[(3S,4S)-3-cyclopropylaminomethyl-4-fluoro-1-pyrrolidinyl]-6,8-difluoro-1-[(1R,2S)-2-fluorocyclopropyl]-1,4-dihydro-4-oxo-3-quinolinecarboxylic acid Using 6,7,8-trifluoro-1-[(1R,2S)-2-fluorocyclopropyl]-1,4-dihydro-4-oxo-3-quinolinecarboxylic acid (301 mg) and (3R,4S)-3-cyclopropylaminomethyl-4-fluoropyrrolidine (190 mg), the same procedure was followed as in Example 23 to give 7-[(3S,4S)-3-cyclopropylaminomethyl-4-fluoro-1-pyrrolidinyl]-6,8-difluoro-1-[(1R,2S)-2-fluorocyclopropyl]-1,4-dihydro-4-oxo-3-quinolinecarboxylic acid as pale yellow crystals (231 mg).

MS(FAB$^+$) m/z: 440(MH$^+$)

elemental analysis (%)

Calcd for $C_{21}H_{21}F_4N_3O_3 \cdot 0.25H_2O$: C, 56.82; H, 4.88; N, 9.47.

Found: C, 56.91; H, 4.67; N, 9.35.

Example 36

Synthesis of 8-chloro-7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-3-quinolinecarboxylic acid Using 8-chloro-6,7-difluoro-1-[(1R,2S)-2-fluorocyclopropyl]-1,4-dihydro-4-oxo-3-quinolinecarboxylic acid (318 mg) and (3R,4S)-3-cyclopropylaminomethyl-4-fluoropyrrolidine (174 mg), the same procedure was followed as in Example 23 to give 8-chloro-7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-3-quinolinecarboxylic acid as a yellow solid (93.6 mg).

MS(FAB$^+$) m/z: 456(MH$^+$)

elemental analysis (%)

Calcd for $C_{21}H_{21}ClF_3N_3O_3 \cdot 0.5H_2O$: C, 54.26; H, 4.77; N, 9.04. Found: C, 54.36; H, 4.54; N, 8.88.

Example 37

Synthesis of 5-amino-1-cyclopropyl-7-[(3S,4S)-3-cyclopropylaminomethyl-4-fluoro-1-pyrrolidinyl]-6-fluoro-1,4-dihydro-8-methoxy-4-oxo-3-quinolinecarboxylic acid 5-amino-1-cyclopropyl-6,7-difluoro-1,4-dihydro-8-methoxy-4-oxo-3-quinolinecarboxylic acid (250 mg), (3R,4S)-3-cyclopropylaminomethyl-4-fluoropyrrolidine (190 mg), triethylamine (0.17 mL) and dimethylsulfoxide (4 mL) were mixed together. The mixture was stirred at 100° C. for 9 hours and was subsequently concentrated under reduced pressure. The resulting residue was purified by silica gel column chromatography (eluant: dichloromethane: methanol=40:1). The eluted yellow solid was recrystallized from ethanol to give 5-amino-1-cyclopropyl-7-[(3S,4S)-3-cyclopropylaminomethyl-4-fluoro-1-pyrrolidinyl]-6-fluoro-1,4-dihydro-8-methoxy-4-oxo-3-quinolinecarboxylic acid as yellow crystals (248 mg).

MS(FAB$^+$) m/z: 449(MH$^+$)

elemental analysis (%)

Calcd for $C_{22}H_{26}F_2N_4O_4$: C, 58.92; H, 5.84; N, 12.49. Found: C, 58.60; H, 5.74; N, 12.39.

Example 38

Synthesis of 5-amino-1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid Using 5-amino-1-cyclopropyl-6,7-difluoro-1,4-dihydro-8-methyl-4-oxo-3-quinolinecarboxylic (79.0 mg) and (3R,4S)-3-cyclopropylaminomethyl-4-fluoropyrrolidine (51.0 mg), the same procedure was followed as in Example 36 to give 5-amino-1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid as a yellow solid (9.6 mg).

MS(FAB$^+$) m/z: 433(MH$^+$)

HRMS(EI)

Calcd for $C_{22}H_{27}F_2N_4O_3$: 433.2051. Found: 433.2086.

Example 39

Synthesis of 5-amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methoxy-4-oxo-3-quinolinecarboxylic acid Using 5-amino-6,7-difluoro-1-[(1R,2S)-2-fluorocyclopropyl]-1,4-dihydro-8-methoxy-4-oxo-3-quinolinecarboxylic) acid (240 mg) and (3R,4S)-3-cyclopropylaminomethyl-4-fluoropyrrolidine (174 mg), the same procedure was followed as in Example 36 to give 5-amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methoxy-4-oxo-3-quinolinecarboxylic acid as a yellow solid (204 mg).

MS(FAB$^+$) m/z: 467(MH$^+$)

elemental analysis (%)

Calcd for $C_{22}H_{25}F_3N_4O_4$: C, 56.65; H, 5.40; N, 12.01. Found: C, 56.63; H, 5.31; N, 11.84.

Example 40

Synthesis of 5-amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methyl-4-oxo-3-quinolinecarboxylic acid Using 5-amino-6,7-difluoro-1-[(1R,2S)-2-fluorocyclopropyl]-1,4-dihydro-8-methyl-4-oxo-3-quinolinecarboxylic acid (20.0 mg) and (3R,4S)-3-cyclopropylaminomethyl-4-fluoropyrrolidine (15.2 mg), the same procedure was followed as in Example 36 to give 5-amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methyl-4-oxo-3-quinolinecarboxylic acid as a yellow solid (9.6 mg).

MS(FAB$^+$) m/z: 451(MH$^+$)

HRMS(EI)

Calcd for $C_{22}H_{26}F_3N_4O_3$: 451.1957. Found: 451.1996.

Example 41

Synthesis of 7-[(3S,4S)-3-cyclopropylaminomethyl-4-fluoro-1-pyrrolidinyl]-6-fluoro-1,4-dihydro-1-(1,1-dimethylethyl)-4-oxo-1,8-naphthyridine-3-carboxylic acid Ethyl 7-chloro-6-fluoro-1,4-dihydro-1-(1,1-dimethylethyl)-4-oxo-1,8-naphthyridine-3-carboxylate (327 mg), (3R,4S)-3-cyclopropylaminomethyl-4-fluoropyrrolidine (174 mg), 1,8-diazabicyclo[5.4.0]undec-7-ene (160 mg) and acetonitrile (5 mL) were mixed together. The reaction mixture was stirred at 80° C. for 1 hour and was concentrated under reduced pressure. The resulting residue was dissolved in dichloromethane (30 mL), washed sequentially with water and saturated brine, dried over anhydrous sodium sulfate, and concentrated under reduced pressure. The resulting residue was purified by silica gel column chromatography (eluant: dichloromethane: acetone=2:1->1:1->dichloromethane: methanol=10:1). The eluted pale yellow solid was dissolved in ethanol (4 mL), followed by addition of a 10% aqueous solution of sodium hydroxide (4 mL), stirring at 60° C. for 70 min, and concentration under reduced pressure. The resulting residue was diluted with water (10 mL), neutralized with 1 mol/L hydrochloric acid (pH 7.5), and extracted with dichloromethane (2×30 mL). The dichloromethane extracts were combined, washed with saturated brine, dried over anhydrous sodium sulfate, and concentrated under reduced pressure. The resulting residue was purified by silica gel column chromatography (eluant: dichloromethane: methanol=10:1) to give 7-[(3S,4S)-3-cyclopropylaminomethyl-4-fluoro-1-pyrrolidinyl]-6-fluoro-1,4-dihydro-1-(1,1-dimethylethyl)-4-oxo-1,8-naphthyridine-3-carboxylic acid as white crystals (141 mg).

MS(FAB$^+$) m/z: 421(MH$^+$)

elemental analysis (%)

Calcd for $C_{21}H_{26}F_2N_4O_3 \cdot 0.5H_2O$: C, 58.73; H, 6.34; N, 13.05. Found: C, 58.83; H, 6.10; N, 13.00.

Example 42

Synthesis of 7-[(3S,4S)-3-cyclopropylaminomethyl-4-fluoro-1-pyrrolidinyl]-6-fluoro-1,4-dihydro-1-(1,1-dimethylethyl)-4-oxo-3-quinolinecarboxylic acid Using ethyl 6,7-difluoro-1,4-dihydro-1-(1,1-dimethylethyl)-4-oxo-3-quinolinecarboxylate (309 mg) and (3R,4S)-3-cyclopropylaminomethyl-4-fluoropyrrolidine (174 mg), the same procedure was followed as in Example 40 to give 7-[(3S,4S)-3-cyclopropylaminomethyl-4-fluoro-1-pyrrolidinyl]-6-fluoro-1,4-dihydro-1-(1,1-dimethylethyl)-4-oxo-3-quinolinecarboxylic acid as pale yellow crystals (91.3 mg).

MS(FAB$^+$) m/z: 420(MH$^+$)

elemental analysis (%)

Calcd for $C_{22}H_{27}F_2N_3O_3$: C, 62.99; H, 6.49; N, 10.02. Found: C, 63.31; H, 6.47; N, 9.95.

Example 43

Synthesis of 7-[(3S,4S)-3-cyclopropylaminomethyl-4-fluoro-1-pyrrolidinyl]-6,8-difluoro-1,4-dihydro-1-(1,1-dimethylethyl)-4-oxo-3-quinolinecarboxylic acid Using ethyl 6,7,8-trifluoro-1,4-dihydro-1-(1,1-dimethylethyl)-4-oxo-3-quinolinecarboxylate (50.0 mg) and (3R,4S)-3-cyclopropylaminomethyl-4-fluoropyrrolidine (29.0 mg), the same procedure was followed as in Example 40 to give 7-[(3S,4S)-3-cyclopropylaminomethyl-4-fluoro-1-pyrrolidinyl]-6,8-difluoro-1,4-dihydro-1-(1,1-dimethylethyl)-4-oxo-3-quinolinecarboxylic acid as a pale yellow powder (25.1 mg).

MS(FAB$^+$) m/z: 438(MH$^+$)

HRMS(EI)

Calcd for $C_{22}H_{27}F_3N_3O_3$: 438.2005. Found: 438.2015.

<Antibacterial Activity>

Test Example

Antibacterial Activity in Vitro

The in-vitro antibacterial activity of the compound of the present invention, as measured by the minimum inhibitory concentration (MIC), was determined by the agar plate dilution technique using Mueller-Hinton agar medium. The technique met the criteria specified by the National Committee for Clinical Laboratory Standard (1997) [NCCLS. Methods for Dilution Antibacterial Susceptibility Tests for Bacteria that grow Aerobically—Forth Edition: Approved Standard m7-A4. NCCLS, Villanova, Pa.]. For *Streptococcus pneumonia* and *Enterococcus*, the MIC values were determined by using Muller-Hinton agar supplemented with 5% defibrinated horse blood. The results are shown in Table 1 below.

[Table 1]

TABLE 1

In vitro antibacterial activity

| Strains | MIC (mg/mL) | | | | |
| --- | --- | --- | --- | --- | --- |
| | Example 1 | Example 2 | Example 3 | Example 4 | Example 5 |
| *S. aureus* Smith | 0.008 | 0.008 | 0.008 | 0.016 | 0.008 |
| *S. aureus* MR5867 | 0.008 | 0.016 | 0.008 | 0.031 | 0.008 |
| *S. aureus* MS16401 | 0.004 | 0.031 | 0.008 | 0.063 | 0.016 |
| *S. pneumoniae* Type III | ≦0.008 | 0.031 | 0.016 | 0.063 | 0.031 |
| *E. faecalis* IID682 | 0.063 | 0.125 | 0.125 | 0.5 | 0.125 |

| Strains | MIC (mg/mL) | | | |
| --- | --- | --- | --- | --- |
| | Example 6 | Example 7 | Example 8 | Example 9 |
| *S. aureus* Smith | 0.031 | 0.031 | 0.031 | ≦0.008 |
| *S. aureus* MR5867 | 0.008 | 0.063 | 0.031 | ≦0.008 |
| *S. aureus* MS16401 | 0.063 | 0.125 | 0.063 | 0.016 |
| *S. pneumoniae* Type III | 0.063 | 0.063 | 0.125 | ≦0.008 |
| *E. faecalis* IID682 | 0.25 | 0.25 | 0.5 | 0.063 |

*S. aureus* MR5867: methicillin-resistant *S. aureus*
*S. aureus* MS16401: quinolone-resistant *S. aureus*

INDUSTRIAL APPLICABILITY

As set forth, the novel 7-(3-cyclopropylaminomethyl-1-pyrrolidinyl)quinolonecarboxylic acid derivatives of the present invention, salts and hydrates thereof serve as safe, strong antibacterial agents that are effective against drug-resistant bacteria that are less susceptible to conventional antibacterial agents.

Thus, the present invention provides novel quinolonecarboxylic acid derivatives as an effective countermeasure against drug-resistant bacteria that are less susceptible to conventional antibacterial agents.

The invention claimed is:

1. A quinolonecarboxylic acid derivative represented by the following formula (I):

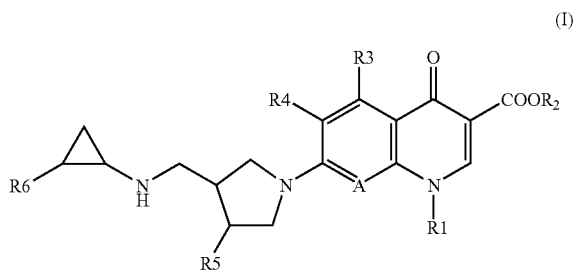

wherein R1 is an alkyl group that has 1 to 6 carbon atoms and may or may not be substituted with 1 or 2 or more halogen atoms, a cycloalkyl group that has 3 to 6 carbon atoms and may or may not be substituted with 1 or 2 or more halogen atoms, or an aryl or heteroaryl group that may or may not be substituted with 1 or 2 or more substituents that are each independently a halogen atom or an amino group; $R_2$ is a hydrogen atom, an alkyl group having 1 to 3 carbon atoms or pharmaceutically acceptable cation, R3 is a hydrogen atom, a halogen atom, a hydroxyl group, an amino group or an alkyl group having 1 to 3 carbon atoms; R4 is a hydrogen atom or a halogen atom; R5 is a fluorine atom; R6 is a hydrogen atom or a fluorine atom; and A is a nitrogen atom or =C-X, where X is a hydrogen atom, halogen atom, or alkyl or alkoxyl group that has 1 to 3 carbon atoms and may or may not be substituted with 1 or 2 or more amino groups, cyano groups or halogen atoms, or a salt thereof.

2. An antibacterial composition containing as an active ingredient the compound according to claim 1 or a salt thereof.

3. A quinolonecarboxylic acid derivative represented by the following formula (I):

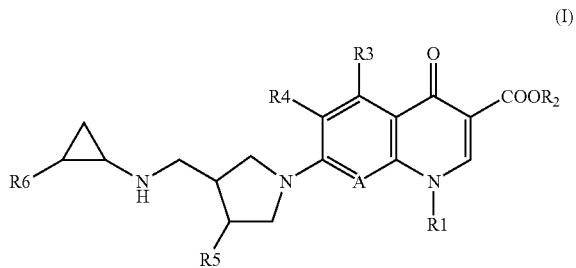

wherein R1 is an alkyl group that has 1 to 6 carbon atoms and may or may not be substituted with 1 or 2 or more halogen atoms, a cycloalkyl group that has 3 to 6 carbon atoms and may or may not be substituted with 1 or 2 or more halogen atoms, or an aryl that may or may not be substituted with 1 or 2 or more halogen atoms; $R_2$ is a hydrogen atom; R3 is a hydrogen atom or an amino group; R4 is a hydrogen atom or a halogen atom; R5 is a fluorine atom; R6 is a hydrogen atom; and A is a nitrogen atom or =C-X, where X is a hydrogen atom, halogen atom, or alkyl or alkoxyl group that has 1 to 3 carbon atoms and may or may not be substituted with 1 or 2 or more halogen atoms, or a salt thereof.

4. The compound according to claim 3, wherein in the formula (I), R1 is a cyclopropyl group, 2-fluorocyclopropyl group, ethyl group, or 2-fluoroethyl group, or a salt thereof.

5. The compound according to claim 3, wherein in the formula (I), R1 is a cyclopropyl group, 2-fluorocyclopropyl group, ethyl group or 2-fluoroethyl group, and R4 is a fluorine atom, or a salt thereof.

6. The compound according to claim 3, wherein in the formula (I), R1 is a cyclopropyl group, 2-fluorocyclopropyl group, ethyl group or 2-fluoroethyl group; R4 is a fluorine atom; and A is a nitrogen atom or =C-X, where X is a hydrogen atom, halogen atom, methoxy group, difluoromethoxy group or methyl group, or a salt thereof.

7. The compound according to claim 3, wherein in the formula (I), R1 is a 2-fluoroethyl group; R4 is a fluorine atom; and A is =C-X, where X is a hydrogen atom, halogen atom, methoxy group, difluoromethoxy group or methyl group, or a salt thereof.

8. The compound according to claim 1, which is selected from the group consisting of:

1 -cyclopropyl-7- [(3 S ,4S)-3-cyclopropylaminomethyl-4-fluoro-1 -pyrrolidinyl]-6-fluoro -1 ,4-dihydro-8-methyl-4-oxo-3-quinolinecarboxylic acid, 7-[(3 S ,4S)-3-cyclopropylaminomethyl-4-fluoro-1 -pyrrolidinyl]-6-fluoro-1-[(1 R, 2S)-2-fluorocyclopropyl]-1,4-dihydro-4-oxo-8-methoxy-3 --quinolinecarboxylic acid, 7-[(3 S,4S)-3-cyclopropylaminomethyl-4-fluoro-1-pyrrolidinyl]-6-fluoro-1-(2-fluoroethyl)-1,4-dihydro-8-methoxy-4-oxo-3-quinolinecarboxylic acid, 8-chloro-1-cyclopropyl-7-[(3S,4S)-3-cyclopropylaminomethyl-4-fluoro-1-pyrrolidinyl]-6-fluoro-1,4-dihydro-4-oxo-3-quinolinecarboxylic acid, 7-[(3S,4S)-3-cyclopropylaminomethyl-4-fluoro-1-pyrrolidinyl]-6,8-difluoro-1-[(1R,2S)-2-fluorocyclopropyl]-1,4-dihydro-4-oxo-3-quinolinecarboxylic acid, 8-chloro-7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-3-quinolinecarboxylic acid, 5-amino-1-cyclopropyl-7-[(3S,4S)-3-cyclopropylaminomethyl-4-fluoro-1-pyrrolidinyl]-6-fluoro-1,4-dihydro-8-methoxy-4-oxo-3-quinolinecarboxylic acid, 5-amino-1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid, 5 -amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methoxy-4-oxo-3-quinolinecarboxylic acid, 5-amino-7-[(3S,4S)-3-cyclopropylaminomethyl-4-fluoro-1-pyrrolidinyl]-6-fluoro-1-[(1R,2S)-2-fluorocyclopropyl]-1,4-dihydro-8-methyl-4-oxo-3--quinolinecarboxylic acid, or a salt thereof.

9. The compound according to claim 1, which is 1-cyclopropyl-7-[(3S,4S)-3-cyclopropylaminomethyl-4-fluoro-1-pyrrolidinyl]-6-fluoro-1,4-dihydro-8-methyl-4-oxo-3-quinolinecarboxylic acid, or a salt thereof.

10. The compound according to claim 1, which is 7-[(3S,4S)-3-cyclopropylaminomethyl-4-fluoro-1-pyrrolidinyl]-6-fluoro-1-[(1R,2S)-2-fluorocyclopropyl]-1,4-dihydro-4-oxo-8-methoxy-3-quinolinecarboxylic acid, or a salt thereof.

11. The compound according to claim 1, which is 7-[(3S,4S)-3-cyclopropylaminomethyl-4-fluoro-1-pyrrolidinyl]-6-fluoro-1-(2-fluoroethyl)-1,4-dihydro-8-methoxy-4-oxo-3-quinolinecarboxylic acid, or a salt thereof.

12. An antibacterial composition containing as an active ingredient the compound according to claim 3 or a salt thereof.

13. An antibacterial composition containing as an active ingredient the compound according to claim 4 or a salt thereof.

14. An antibacterial composition containing as an active ingredient the compound according to claim 5 or a salt thereof.

15. An antibacterial composition containing as an active ingredient the compound according to claim 6 or a salt thereof.

16. An antibacterial composition containing as an active ingredient the compound according to claim 7 or a salt thereof.

17. An antibacterial composition containing as an active ingredient the compound according to claim 8 or a salt thereof.

18. An antibacterial composition containing as an active ingredient the compound according to claim 9 or a salt thereof.

19. An antibacterial composition containing as an active ingredient the compound according to claim 10 or a salt thereof.

20. An antibacterial composition containing as an active ingredient the compound according to claim 11 or a salt thereof.

* * * * *